US012685844B2

(12) United States Patent
Tal

(10) Patent No.: US 12,685,844 B2
(45) Date of Patent: Jul. 21, 2026

(54) GUIDEWIRE WITH ELASTICALLY ARTICULATABLE TIP

(71) Applicant: Embrace Medical Ltd, Tel Aviv (IL)

(72) Inventor: Michael Gabriel Tal, Tel Aviv (IL)

(73) Assignee: Embrace Medical Ltd., Tel Aviv (IL)

( * ) Notice: Subject to any disclaimer, the term of this patent is extended or adjusted under 35 U.S.C. 154(b) by 1133 days.

(21) Appl. No.: 17/767,553

(22) PCT Filed: Oct. 16, 2020

(86) PCT No.: PCT/US2020/055991
§ 371 (c)(1),
(2) Date: Apr. 8, 2022

(87) PCT Pub. No.: WO2021/076894
PCT Pub. Date: Apr. 22, 2021

(65) Prior Publication Data
US 2022/0401706 A1       Dec. 22, 2022

Related U.S. Application Data

(60) Provisional application No. 62/915,973, filed on Oct. 16, 2019.

(51) Int. Cl.
*A61M 25/09*       (2006.01)
*A61M 39/02*       (2006.01)

(52) U.S. Cl.
CPC ...... *A61M 25/09* (2013.01); *A61M 25/09041* (2013.01); *A61M 39/0208* (2013.01); *A61M 2025/09175* (2013.01); *A61M 2025/09191* (2013.01); *A61M 2039/0235* (2013.01)

(58) Field of Classification Search
CPC ............ A61M 25/09; A61M 25/09041; A61M 39/0208; A61M 2025/09175; A61M 2025/09191; A61M 2025/09083; A61M 2025/0915
See application file for complete search history.

(56) References Cited

U.S. PATENT DOCUMENTS

| | | | |
|---|---|---|---|
| 1,879,249 A | 9/1932 | Coy | |
| 2,717,599 A | 9/1955 | Jennie | |
| 2,746,454 A | 5/1956 | Sorensen | |
| 3,521,620 A | 7/1970 | Cook | |

(Continued)

FOREIGN PATENT DOCUMENTS

| | | |
|---|---|---|
| CN | 103845785 A | 6/2014 |
| CN | 116615266 A | 8/2023 |

(Continued)

OTHER PUBLICATIONS

Decision of Rejection mailed on Dec. 4, 2024 in JP 2022-520864.

(Continued)

*Primary Examiner* — Alex M Valvis
*Assistant Examiner* — Yasmeen S Warsi
(74) *Attorney, Agent, or Firm* — Veros Legal Solutions, LLP

(57) ABSTRACT

A guidewire for vascular access has an elastically articulatable tip configured to minimize risk of vessel wall damage during initial insertion of the guidewire into the vasculature of a patient. The guidewire may have a local flexible portion in a tip segment of the guidewire and/or a core thereof.

31 Claims, 13 Drawing Sheets

(56) References Cited

U.S. PATENT DOCUMENTS

| | | | |
|---|---|---|---|
| 4,456,017 A | 6/1984 | Miles | |
| 4,661,300 A | 4/1987 | Daugherty | |
| 4,716,757 A | 1/1988 | McGregor et al. | |
| 4,904,433 A | 2/1990 | Williamitis | |
| 4,919,605 A | 4/1990 | Kousai et al. | |
| 5,057,083 A | 10/1991 | Gellman | |
| 5,102,324 A | 4/1992 | Bullard et al. | |
| 5,111,829 A * | 5/1992 | Alvarez de Toledo .. | A61B 1/01 |
| | | | 600/585 |
| 5,341,818 A | 8/1994 | Abrams et al. | |
| 5,352,205 A | 10/1994 | Dales et al. | |
| 5,365,942 A | 11/1994 | Shank | |
| 5,478,328 A | 12/1995 | Silverman et al. | |
| 5,484,565 A | 1/1996 | Larsen et al. | |
| 5,497,786 A | 3/1996 | Urick | |
| 5,531,701 A | 7/1996 | Luther | |
| 5,716,572 A | 2/1998 | Lesiczka et al. | |
| 5,807,279 A | 9/1998 | Viera | |
| 5,843,356 A | 12/1998 | Patel et al. | |
| 5,857,464 A | 1/1999 | Desai | |
| 5,865,767 A | 2/1999 | Frechette et al. | |
| 5,957,865 A | 9/1999 | Backman et al. | |
| 5,985,195 A | 11/1999 | Muskatello | |
| RE36,628 E | 3/2000 | Sagae et al. | |
| 6,113,557 A | 9/2000 | Fagan et al. | |
| 6,596,011 B2 | 7/2003 | Johnson et al. | |
| 6,638,266 B2 | 10/2003 | Wilson et al. | |
| 6,740,277 B2 | 5/2004 | Howell et al. | |
| 6,979,318 B1 | 12/2005 | McDonald et al. | |
| 7,029,467 B2 | 4/2006 | Currier et al. | |
| 7,762,962 B2 | 7/2010 | Mishima | |
| 7,959,595 B2 | 6/2011 | Melsheimer et al. | |
| 8,092,395 B2 | 1/2012 | Lupton et al. | |
| 8,142,416 B2 | 3/2012 | Stauber | |
| 8,936,581 B2 | 1/2015 | Bihlmaier | |
| 8,986,225 B2 | 3/2015 | Folk | |
| 9,078,994 B2 | 7/2015 | Rosenman et al. | |
| 9,757,536 B2 | 9/2017 | Abt et al. | |
| 9,987,423 B2 | 6/2018 | Kuracina et al. | |
| 9,987,468 B2 | 6/2018 | Bagwell et al. | |
| 10,384,039 B2 | 8/2019 | Ribelin et al. | |
| 10,441,746 B2 | 10/2019 | Besselink | |
| 10,478,592 B2 | 11/2019 | Shevgoor | |
| 10,610,668 B2 | 4/2020 | Burkholz et al. | |
| 10,820,923 B2 | 11/2020 | Govari | |
| 10,987,489 B2 | 4/2021 | Von Segesser | |
| 2002/0082523 A1 | 6/2002 | Kinsella et al. | |
| 2003/0163064 A1 | 8/2003 | Vrba et al. | |
| 2004/0167436 A1 | 8/2004 | Reynolds et al. | |
| 2004/0167437 A1 | 8/2004 | Sharrow et al. | |
| 2005/0049690 A1 | 3/2005 | Boismier et al. | |
| 2008/0281156 A1 * | 11/2008 | Makower ............. | A61B 17/282 |
| | | | 600/118 |
| 2009/0076435 A1 | 3/2009 | Melsheimer et al. | |
| 2010/0217234 A1 | 8/2010 | Grovender et al. | |
| 2012/0065569 A1 | 3/2012 | Steegers et al. | |
| 2014/0163420 A1 | 6/2014 | Kosugi | |
| 2015/0038908 A1 | 2/2015 | Antonucci | |
| 2016/0256667 A1 | 9/2016 | Ribelin et al. | |
| 2017/0259041 A1 | 9/2017 | Lenker | |
| 2019/0030290 A1 | 1/2019 | Ginster | |
| 2019/0038876 A1 | 2/2019 | Isaacson et al. | |
| 2019/0038877 A1 | 2/2019 | Isaacson et al. | |
| 2020/0188632 A1 | 6/2020 | Burkholz et al. | |
| 2020/0330729 A1 | 10/2020 | Petitpierre et al. | |
| 2022/0211981 A1 | 7/2022 | Darbellay et al. | |
| 2022/0401706 A1 | 12/2022 | Tal | |
| 2023/0398331 A1 | 12/2023 | Tal | |

FOREIGN PATENT DOCUMENTS

| | | |
|---|---|---|
| IN | 202227020741 A | 12/2022 |
| JP | H04108555 A | 9/1992 |
| JP | 2005169012 A | 6/2005 |
| JP | 2006055674 A | 3/2006 |
| JP | 2012205800 A | 10/2012 |
| JP | 2014113177 A | 6/2014 |
| JP | 2012205800 B | 6/2015 |
| JP | 2016002210 A | 1/2016 |
| JP | 2018519015 A | 7/2018 |
| JP | 2019111083 A | 7/2019 |
| JP | 2019150439 A | 9/2019 |
| WO | 2009131583 A1 | 10/2009 |
| WO | 2010110132 A1 | 9/2010 |
| WO | 2014162389 A1 | 10/2014 |
| WO | 2019081962 A1 | 5/2019 |
| WO | 2021076894 A1 | 4/2021 |
| WO | 2022081201 A1 | 4/2022 |

OTHER PUBLICATIONS

Extended European Search Report mailed on Jan. 10, 2025 in EP 21880704.8.

Notice of Allowance mailed on Feb. 18, 2025 in CA 3156632.

Office Action mailed on Jan. 27, 2025 in JP 2023-523198.

Partial Supplementary European Search Report mailed on Oct. 14, 2024 in EP 21880704.8.

Supplementary European Search Report mailed on Jan. 28, 2025 in EP 21880704.8.

International Search Report and Written Opinion mailed Feb. 9, 2021 in PCT/US2020/055991.

International Search Report and Written Opinion mailed Sep. 14, 2021 in PCT/US2021/027280.

Extended European Search Report mailed on Feb. 15, 2024 in EP 21753965.9.

Final Office Action mailed on May 1, 2024 in JP 2022-520864.

International Preliminary Report on Patentability received for WO Patent Application Serial No. PCTUS2021027280 dated Apr. 27, 2023, 10 pages.

International Search Report and Written Opinion mailed on Sep. 14, 2021 in PCT/US2021/027280.

Invitation to Pay Additional Fees mailed Nov. 25, 2020 in International Patent Application No. PCT/US2020/055991.

Office Action mailed on Apr. 3, 2024 in CA 3156632.

Communication pursuant to Article 94(3) EPC mailed on Dec. 15, 2025 in EP 20876438.1.

Examination Report mailed on Apr. 2, 2025 in AU 2020368478.

International Preliminary Report on Patentability, mailed Apr. 13, 2023.

Office Action mailed on Aug. 1, 2025 in CN 202180085436.3.

Office Action mailed on Aug. 27, 2025 in JP 2023-523198.

Supplementary European Search Report mailed Jan. 16, 2024.

* cited by examiner

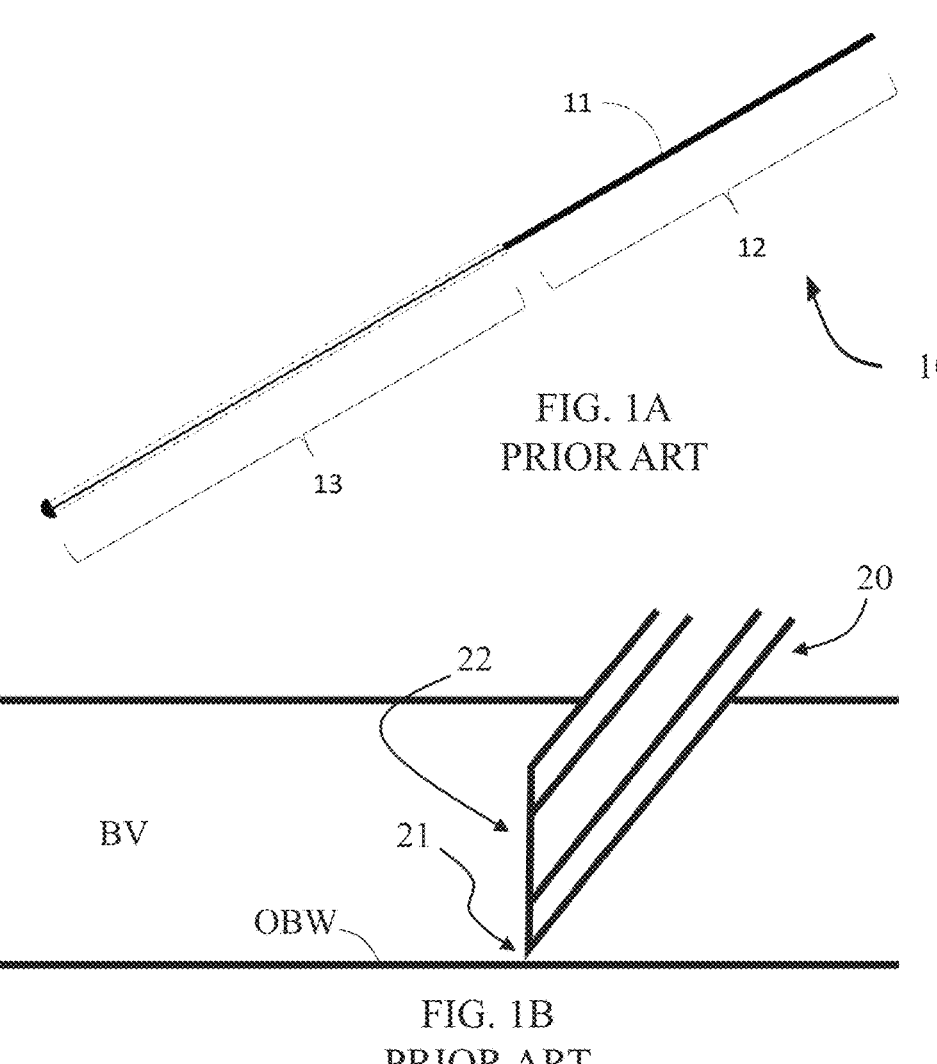
FIG. 1A
PRIOR ART
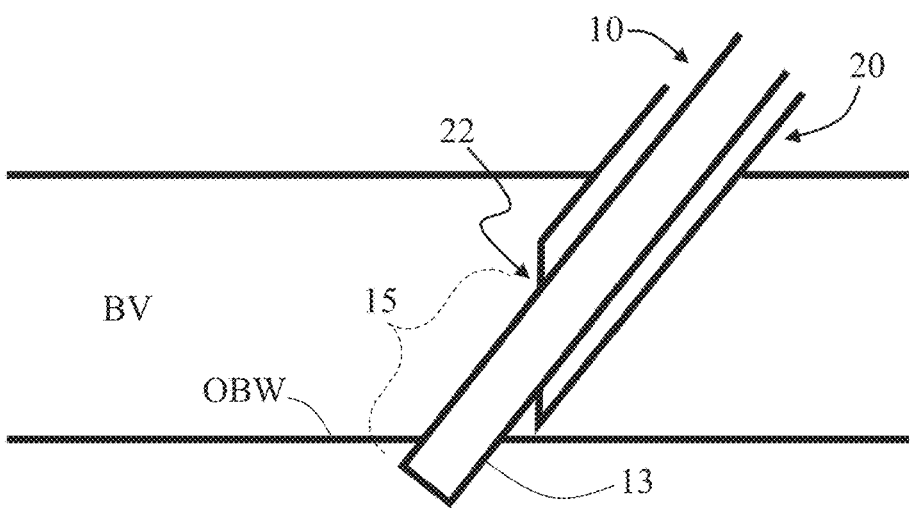
FIG. 1B
PRIOR ART
FIG. 1C
PRIOR ART

GUIDEWIRE WITH ELASTICALLY ARTICULATABLE TIP

FIELD

The present disclosure, in some embodiments thereof, relates to devices and methods for accessing a blood vessel, and more particularly, but not exclusively, to guidewires and/or vascular access kits.

BACKGROUND

The Seldinger technique is currently the preferred approach to access blood vessels, in which a needle penetrates into the vessel, and, once it is verified that the needle tip is inside the vessel, a guidewire is inserted through the needle and maneuvered to the desired place in the blood vessel, then the needle is taken out and a catheter can be positioned over the guidewire at the designated area.

Unintended perforation or dissection of the blood vessel is not an uncommon failure when using Seldinger technique. If the needle tip is positioned near the blood vessel centerline, and in an acute angle thereto, the guidewire should exit the needle tip without causing unnecessary perforation as described. However, in many cases the needle tip is too close to the opposing vessel wall, or even partly penetrated thereto, and/or the access angle of the needle relative to the blood vessel is too shallow (e.g., greater than about 60°), although the operator may obtain blood return via the inserted needle, supposedly a positive indication for a correct needle placement. However, the guidewire is forcefully pushed into the blood vessel through the needle, the tip of the guidewire can perforate the vessel wall and/or dissect vessel wall layers, especially since that guidewires are designed for sufficient pushability for allowing its advancing through the needle and the blood vessel.

The problem of unintentional penetration (e.g., perforation and/or dissection) of blood vessel wall when forming access into the blood vessel is especially noticeable in veins, in which the walls are thin and flexible, such that the operator may not sense any resistance from the needle and continue advancing the guidewire out of the vein through the unintentionally formed penetration opening.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

The present disclosure, in some embodiments thereof, relates to devices and methods for accessing a blood vessel, and more particularly, but not exclusively, to guidewires and/or vascular access kits configured to prevent unintentional puncture of blood vessel wall when forming access into a blood vessel.

In one implementation, a guidewire comprises a guidewire body ending with a tip segment comprising a local flexing portion, a front portion extending distally from the flexing portion, and a rear portion extending proximally from the flexing portion. The flexing portion is configured with resistance to bending substantially smaller than resistance to bending of the remainder of the guidewire body, such that the front portion is elastically articulatable relative to the rear portion about the flexing portion. A guidewire for transluminal routing of artifacts in a blood vessel, comprising:

In another implementation, a guidewire comprises a guidewire body that comprises a guidewire proximal segment, a tip segment and a guidewire intermediate segment extending between the guidewire proximal segment and the tip segment. The resistance to bending of the guidewire intermediate segment along most or all the length thereof is smaller than resistance to bending along most or all length of the guidewire proximal segment. The tip segment includes a local flexing portion having resistance to bending substantially smaller than the resistance to bending of the guidewire intermediate segment, of a front portion of the tip segment extending to distally from the local flexing portion, and of a rear portion of the tip segment extending proximally from the local flexing portion, thereby affecting localized elastic articulatability of the front portion of the tip segment relative to the rear portion of the tip segment and/or to the guidewire intermediate segment.

In another implementation, a guidewire comprises an elongated core comprising a tip segment, wherein the tip segment terminates at a distal end for insertion into a vessel of a patient. The tip segment has a bending resistance profile configured to cause the tip segment to transition from a substantially straight configuration to a folded configuration in response to an insertion force pushing the distal end against a vessel wall, wherein the folding occurs without the distal end penetrating substantially into the tissue of the vessel wall against which the distal end is being pushed.

In another implementation, a guidewire comprises a tip segment terminating in a guidewire distal end, wherein the tip segment is characterized by a bending resistance profile, wherein the bending resistance profile comprises a first region characterized by a first bending resistance, a second region characterized by a second bending resistance, and a third region characterized by a third bending resistance, wherein the second region is positioned between the first region and the third region, wherein the second bending resistance is less than both the first bending resistance and the third bending resistance, wherein the first region includes the guidewire distal end, and wherein the first region, the second region, and at least a portion of the third region are contiguous and are all located 20 mm or less from the guidewire distal end.

In another embodiment, a kit comprises a guidewire according to any novel guidewire embodiment described herein and a needle comprising a beveled opening distally adjacent to a distal needle tip. The beveled opening has a length configured such that when the front portion of the tip segment is pushed against a blood vessel wall, the front portion is configured to articulate about the flexing portion upon axial protrusion from the beveled opening.

In another implementation, a method of inserting a guidewire into a vessel of a patient comprises inserting an opening of a lumen into a vessel of a patient, inserting a distal end of a guidewire into the lumen until the distal end protrudes from the opening, contacts the lower vessel wall, and forms a catch point thereon. The method further comprises applying an insertion force to a proximal portion of the guidewire sufficient to (1) cause a tip segment of the guidewire extending proximally from the distal end of the guidewire to buckle and thereby release the distal end of the guidewire from the catch point, and (2) to elastically return the tip segment of the guidewire to an unbuckled state with the guidewire distal end pointing in an intended navigation direction inside the vessel.

In any embodiment of guidewire, kit, or method described herein, any one or more of the following recited features may be provided in any combination:

the flexing portion may be about 3 mm or less in length and distant about 5 mm or less from a distal end of the guidewire body;

the flexing portion may be configured to elastically recover a pre-articulated orientation and/or alignment of the front portion with the rear portion when the front portion is released from being forcefully articulated relative to the rear portion;

the flexing portion may be configured to facilitate and/or cause elastically recoverable buckling of the rear portion of the tip segment upon longitudinal compression of the guidewire body against a blood vessel wall, when the front portion of the tip segment is forcefully articulated relative to the rear portion;

the guidewire may comprise an elastic core member extending along most or all length of the guidewire body, wherein the core member incorporates the flexing portion along the tip segment;

the elastic core member may comprise a widening proximally to the flexing portion and is substantially greater in diameter along the front portion from the widening to the distal end of the guidewire body;

the elastic core member along the rear portion may be substantially similar in diameter to the flexing portion;

the flexing portion may be configured to facilitate and cause elastically recoverable buckling of the rear portion of the tip segment upon longitudinal compression of the guidewire body against a blood vessel wall, when the front portion of the tip segment is forcefully articulated relative to the rear portion;

the tip segment may be 20 mm or less in total length;

the tip segment may be 10 mm or less in total length;

the tip segment may be 5 mm or less in total length;

the flexing portion may include at least one of a slit, a joint, an indentation, a coiled segment, or any combination thereof;

the guidewire may comprise an elastic core member extending along most or all the length of the guidewire body;

the core member may have a reduced diameter from a first core member diameter proximal to a narrowing to a second core member diameter being smaller than the first core member diameter distal to the narrowing;

the core member may comprise a widening proximally to the flexing portion, wherein the widening increases core member diameter from a third core member diameter proximal to the widening to a fourth core member diameter being greater than the third core member diameter distal to the widening;

a third core member diameter may be equal to or smaller than the second core member diameter and/or the fourth core member diameter may be substantially equal to the first core member diameter;

the core member may be at least partially embedded in a matrix of flexible material between the narrowing and the widening of the core member, such that overall diameter of the guidewire body along most or all length of the guidewire intermediate segment is substantially equal to the first core member diameter;

the core member may be at least partially covered with a cylindrical coiled member between the narrowing and the widening of the core member, such that overall diameter of the guidewire body along most or all length of the guidewire intermediate segment is substantially equal to the first core member diameter;

the coiled member may be formed of a spring and/or elastic metal alloy and is fixated to the core member at or adjacent to the narrowing and/or at or adjacent to the widening;

the core member may incorporate the flexing portion along the tip segment;

the flexing portion may have a length along the guidewire body that is equal to or smaller than 5 mm;

the flexing portion may have a length along the guidewire body of equal to or smaller than 3 mm;

the flexing portion may have a length along the guidewire body or equal to or smaller than 1 mm;

the core member may be formed of a selectively heat treated shape memory alloy;

the heat treatment may be configured to elevate a temperature of a portion of the target length to about 500° C. or less during a period of about 1 minute or less.

the heat treatment may precede fixation of a distal end of a coiled member to the core member distally to the flexing portion, optionally by way of welding, riveting, soldering or brazing;

the resistance to bending of the flexing portion may increase when the angle formed between the front and the rear portions of the tip segment reduces;

a minimally allowed articulation angle between the front and the rear portions may be between 150° and 90°;

a minimally allowed articulation angle may be between 135° and 95°;

the resistance to bending of the flexing portion may be smaller than resistance to penetration of a wall of the blood vessel with the tip segment when the front and the rear portions of the tip segment are aligned;

the resistance to bending of the flexing portion may be greater than a resistance to buckling of the rear portion of the tip segment, when the front and the rear portions of the tip segment form the minimally allowed articulation angle therebetween;

a total length of the flexing portion may be 0.5 mm or less.

a diameter of the flexing portion may be substantially equal to diameter of the rear portion and/or to the guidewire intermediate segment;

the center of the flexing portion may be 5 mm or less from a distal end of the guidewire body;

the center of the flexing portion may be 1 mm or less from a distal end of the guidewire body;

the folding may be capable of causing a portion of the tip segment containing the distal end to transition from pointing in an intended guidewire navigation direction to pointing away from the intended guidewire navigation direction;

the folding may be capable of releasing the distal end of the guidewire from a catch point in the vessel wall;

the bending resistance may be elastic such that the folding is elastically recoverable to return the tip portion to the substantially straight configuration;

the flexing portion may be configured to elastically recover a pre-articulated orientation and/or alignment of the front portion with the rear portion when the front portion is released from being forcefully articulated relative to the rear portion;

the flexing portion may be configured to facilitate and/or cause elastically recoverable buckling of the rear portion of the tip segment upon longitudinal compression of the guidewire body against a blood vessel wall, when the front portion of the tip segment is forcefully articulated relative to the rear portion;

the center of the second region may be located less than 10 mm from the distal end;

the center of the second region may be located less than 5 mm from the distal end;

the second region may span a length along the guidewire of less than 5 mm;

the second region may span a length along the guidewire of less than 3 mm;

the beveled opening may be equal to or greater by up to 2 mm than the front portion in length;

the beveled opening may be equal to or smaller by up to 2 mm than the front portion in length;

the applied insertion force may be insufficient to cause the distal end of the guidewire to significantly penetrate the tissue of the vessel wall at the catch point;

the applied force may be sufficient to cause the tip segment to bend in a first location before buckling at a second location that is proximal to the first location.

All technical or/and scientific words, terms, or/and phrases, used herein have the same or similar meaning as commonly understood by one of ordinary skill in the art to which the disclosure pertains, unless otherwise specifically defined or stated herein. In case of conflict, the patent specification, including definitions, will control.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Some embodiments of the present disclosure are herein described, by way of example only, with reference to the accompanying drawings. With specific reference now to the drawings in detail, it is stressed that the particulars shown are by way of example and for purposes of illustrative description of some embodiments of the present disclosure. In this regard, the description taken together with the accompanying drawings make apparent to those skilled in the art how some embodiments of the present disclosure may be practiced.

FIGS. 1A-1C schematically illustrate a side view of a prior art guidewire (FIG. 1A) and cross-sectional side views the guidewire delivered into a blood vessel using a traditional Seldinger technique (FIGS. 1B-1C);

DETAILED DESCRIPTION

Figure 2A:
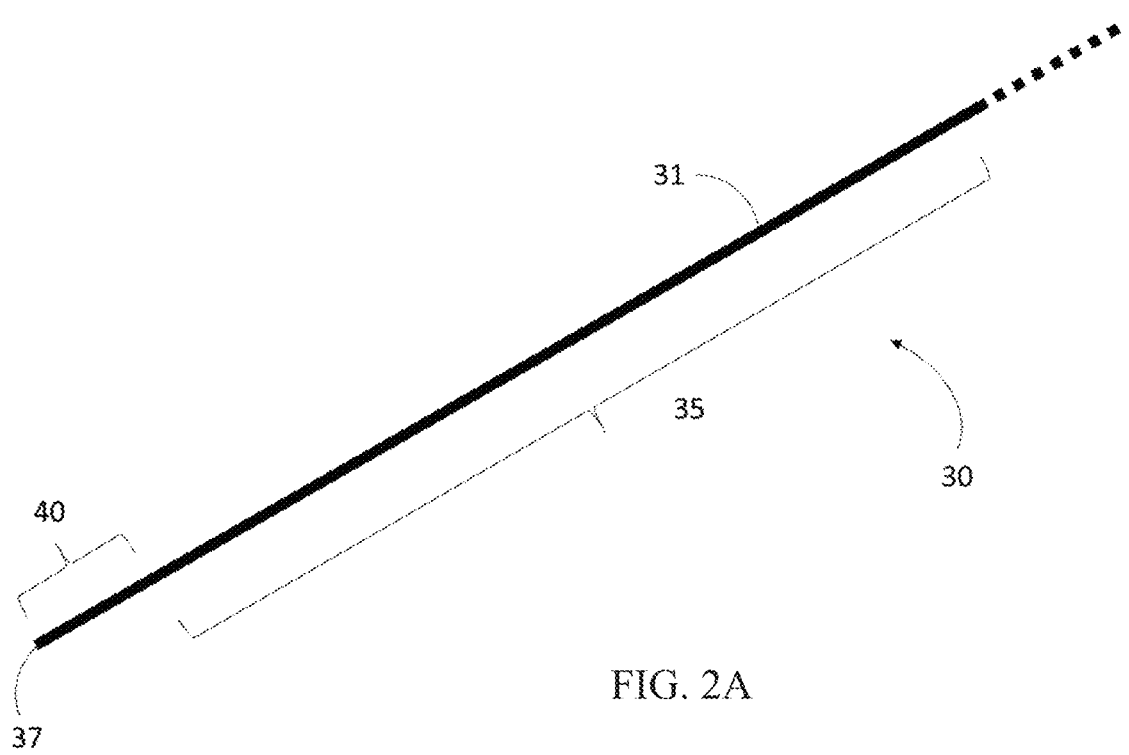
FIGS. 2A-2C schematically illustrate several views of an exemplary guidewire comprising an elastically articulatable tip portion, according to some embodiments.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

The present disclosure, in some embodiments thereof, relates to devices and methods for accessing a blood vessel, and more particularly, but not exclusively, to guidewires and/or vascular access kits configured to prevent unintentional puncture of blood vessel wall when forming access into a blood vessel. The term "guidewire" (or "guide wire") refers to any thin member configured for facilitating a chosen route in bodily vessels for passing artifacts therealong to a target location, such as by way of passing a sheath, a cannula, a catheter or any other device over the guidewire into a cavity or vessel. In some embodiments, the term guidewire is inclusive of vascular access wires which are used in the process of forming a vascular access, optionally prior to insertion of another guidewire prescribed for routing artifacts deeper in the patient's vasculature, for example.

FIG. 1A schematically illustrates a prior art guidewire 10 having an elongated guidewire body 11, which, as in common commercially available guidewires, includes a proximal segment 12 adjoining a distal segment 13. As known in the art, the structural member forming proximal segment 12 and outer diameter thereof, may narrow at a point along the length thereof (or gradually along the entire length) to make the guidewire easier to push through bends and the like in the patient's vasculature. The distal segment 13 may be covered with a coiled member or an elastic coating or matrix. Although this design concept was developed in order to improve flexibility and maneuverability of the guidewires' distal segment when pushed inside blood vessel, while preventing buckling thereof, it has not overcome issues related to initial guidewire access into the blood vessel.

As shown in FIGS. 1B-1C, representing part of a traditional Seldinger technique, a needle 20 is first inserted into blood vessel BV until a needle tip 21 thereof is positioned adjacent to opposing blood vessel wall OBW. Then, distal segment 13 of guidewire 10 is introduced into blood vessel
BV via needle 20. Although distal segment 13 is considered
relatively flexible in relevant publications, the initial pro-
truding length 15 of distal segment 13, emerging from
beveled opening 22 of needle 20 adjacent tip 21, is too short
to flex since that its resistance to bending is greater than
blood vessel walls OBW resistance to penetration of
guidewire 10 with distal end 16 thereof, as shown in FIG.
1C.

Figures 2B, 2C:
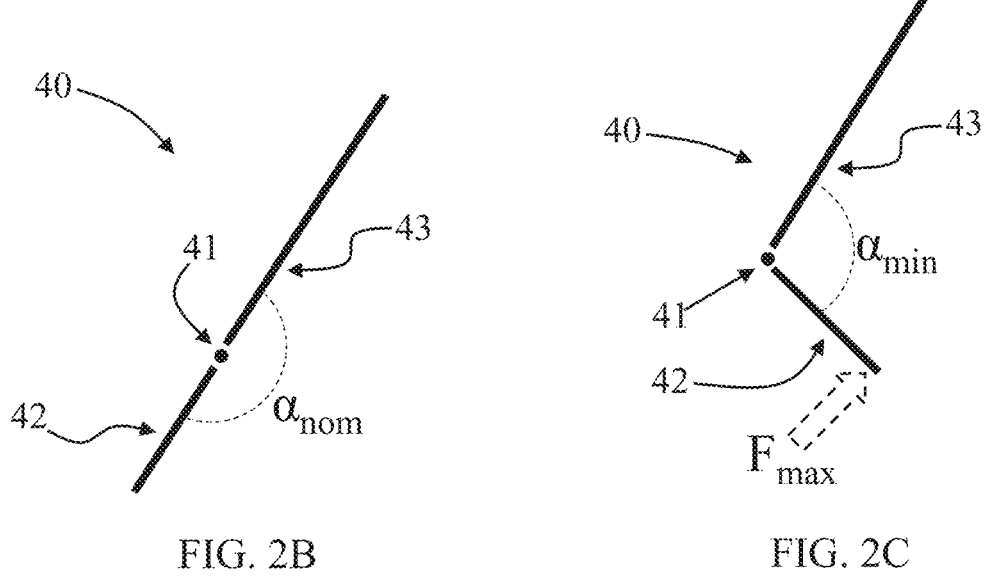

FIGS. 2A-2C schematically illustrate several views of an
exemplary guidewire 30 configured for transluminal routing
of artifacts in a blood vessel. As shown in FIG. 2A,
guidewire 30 includes a guidewire body 31 having a
guidewire distal portion and/or core member thereof that
comprises an intermediate segment 35 and a tip segment 40.
Guidewire intermediate segment 35 is part of distal segment
of prior art guidewires described above, and it may have
greater flexibility and/or elasticity relative to a guidewire
proximal segment.

Figure 3A:
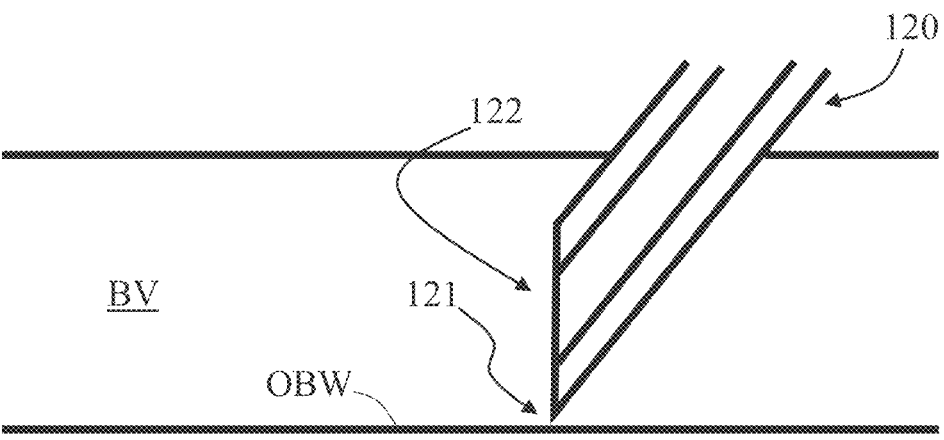
FIGS. 3A-3E schematically illustrate several views representing possible scenarios in execution of a method for delivering the exemplary guidewire of FIG. 2 using an exemplary vascular access technique, according to some embodiments.
Figure 3B:
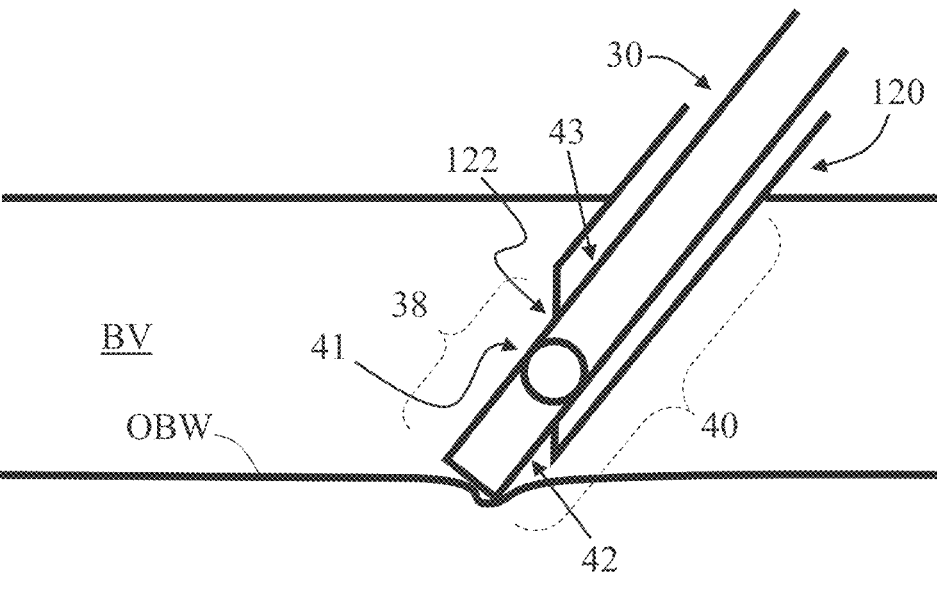

Tip segment 40 has a total length which is at least the
length of an initial protrusion length 38 of guidewire 30 (as
shown in FIG. 3B) which is prescribed for emerging through
an access needle (e.g., needle 20 shown in FIG. 1B) for
accessing into the blood vessel, optionally tip segment 40 is
twice to three-times in length than initial protruding length
38. Tip segment 40 is optionally equal to or less than about
20 mm in total length, optionally about 10 mm or less,
optionally about 5 mm or less, optionally between about 1
mm and about 4 mm in total length. FIG. 2B is a magnified
schematic illustration of a portion of tip segment 40. Tip
segment 40 is characterized by a bending resistance profile
such that different parts of the tip segment have different
bending resistance. The bending resistance profile may
include a flexing portion (e.g., point, area, length, or span)
41 configured to facilitate and/or cause relative elastic
articulation (shown in FIG. 2C) of adjacent front portion 42
(which extend proximally from flexing portion 41) and rear
portion 43 (which extend distally from flexing portion 41) of
tip segment 40, upon such a longitudinal compression. The
center of the flexing portion 41 may advantageously be
about 5 mm or less from the guidewire distal end 37,
optionally particularly about 1 mm or less. Articulation may
be in the form of bending, flexing, or pivoting around or
within flexing portion 41, in one direction, several specific
directions or in any direction, for example. Flexing portion
41 optionally includes at least one of a slit, a joint, an
indentation, a coiled segment, or any combination thereof.
Alternatively, flexing portion 41 may be conditioned differ-
ently or additionally to other portions of tip segment 40,
such as by way of heat treatment and/or chemical treatment,
optionally without affecting change in dimension (e.g.,
diameter) to the flexing portion 41. Elastic articulation
means that once a flexing force ceases, or reduces to below
a certain threshold, the adjacent portions 42 and 43 and/or
flexing portion 41 will recover to a no-stress or less-stressed
relative positioning. Optionally, front portion 42 and rear
portion 43 of tip segment 40 are normally aligned with each
other, meaning that after elastic articulation and cease of
flexing (articulating) force, flexing portion 41 and/or front
and rear portions 42 and 43 will tend to recover elastically
towards relative alignment of front portion 42 with rear
portion 43 due to internal stresses generated by the recov-
ering elastic articulation of flexing portion 41.

In some embodiments, a region of the tip segment (which
may be referred to as the second region) comprising flexing
portion 41 has smaller resistance to bending than front and
rear portions 42 and 43 of the tip segment 40 (which may be referred to as the first and third regions respectively), so that
by applying bending forces or moments thereto, front por-
tion 42 will articulate (e.g., revolve) relative to rear portion
43 which optionally remains substantially unflexed or even
straighten relative to reminder of guidewire body 31. When
unstressed, front and rear portions 42 and 43 of tip segment
40 are optionally normally aligned with each other or form
nominal positioning angle $\alpha_{nom}$ therebetween which is
optionally greater than 135°, optionally particularly greater
than 150°, optionally particularly about 180° (i.e., front and
rear portions 42 and 43 are normally straighten one with
each other). The resistance to bending of the flexing portion
41 optionally increases when front and rear portions 42 and
43 shift from the nominal or unstressed relative positioning.
In some embodiments, guidewire 30 is configured and/or
prescribed for a minimally allowed articulation angle $\alpha_{min}$
between front and rear portions 42 and 43, when a maxi-
mally allowed force $F_{max}$ is applied, which is optionally
greater than 90°; optionally between about 150° and about
90°; optionally particularly between about 135° and about
95°.

In some embodiments, the (minimal) resistance to bend-
ing of flexing portion 41—when adjacent portions 42 and 43
of tip segment 40 are aligned—is smaller than the minimal
axial force sufficient to cause penetration of tip segment 40
into a blood vessel wall (such as internal wall structure of a
vein) when the distal end of guidewire 30 presses against it
(as shown in FIG. 3B, for example), and it gradually
increases with extent of articulation. This feature can be
found advantageous for assisting in prevention of unin-
tended perforations of the host blood vessel wall such as
during introduction of guidewire 30 into the blood vessel.

Optionally and additionally, when the articulation angle
reaches closer to minimally allowed articulation angle $\alpha_{min}$,
the increased resistance to bending becomes greater than
resistance to buckling of the remainder nonarticulated part
of tip segment 40 which comprises rear portion 43. This
feature is advantageous for directing tip segment 40 anteri-
orly, away from the blood vessel wall and the access needle,
and possibly opposite to the direction of intended navigation
of the guidewire through the vasculature of the patient when
guidewire 30 is further pushed into the blood vessel, thereby
further assisting in preventing or diminishing harm (e.g.,
dissection) to the blood vessel wall in proximity to the
access needle, optionally even after preliminary uninten-
tional penetration of the blood vessel wall.

In some embodiments, guidewire 30 is provided in a kit
comprising at least other vascular access members such as
needle 120 shown in FIG. 3A. The kit may also include a
sheath and/or a dilator. Needle 120 includes a beveled
opening 122 distally adjacent to a distal needle tip 121.
Needle 120 and guidewire 30 are configured such that
beveled opening 122 is similar in length to front portion 42
of tip segment 40, such that, when the guidewire body is
pushed against a blood vessel wall, front portion 42 is
configured to articulate about flexing portion 41 upon axial
protrusion relative to distal needle tip 121. In some embodi-
ments, beveled opening 122 is equal to or greater by up to
2 mm than front portion 42 in length. Alternatively, beveled
opening 122 can be equal to or smaller by up to 2 mm than
front portion 42 in length.

Reference is now made to FIGS. 3A-3E which schemati-
cally illustrate several views representing possible scenarios
in execution of a method for delivering guidewire 30,
optionally as part of an exemplary vascular access tech-
nique. In some embodiments, this vascular access technique
is applicable using different types of access needles, such as needle 20. However, in some instances it may be further advantageous to apply this exemplary technique using needle 120 to maximize the outcomes of the method and/or to further diminish or prevent potential unintentional penetration of a blood vessel wall.

Needle 120 is first inserted into blood vessel BV generally in a direction of intended guidewire navigation until needle tip 121 is positioned adjacent to opposing blood vessel wall OBW (FIG. 3A). Then, guidewire 30 is introduced into needle 120 such that tip segment 40 protrudes via beveled opening 122 across needle tip 121 (FIG. 3B) while possibly causing small indentation or compression in the opposing blood vessel wall OBW to produce a catch point where the guidewire tip becomes restrained from further motion in the intended navigation direction. The indentation or compression may have a magnitude dependent on the pressing force applied thereto and tissue elasticity and resistance to compression. At this stage, flexing portion 41 is already protruding at least in part anteriorly (distally) from needled beveled opening 122.

Figure 3C:
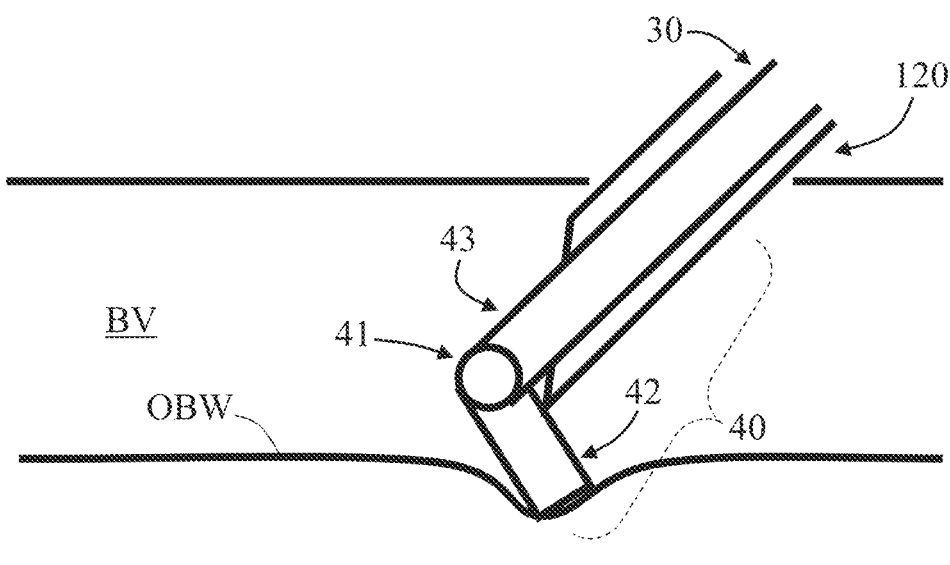

FIG. 3C shows guidewire 30 after it is further pushed into blood vessel BV. As both—the longitudinal compression in tip segment 40 and resistance to compression of opposing blood vessel wall OBW—elevate, the moment acting on flexing portion 41 eventually exceeds its initial resistance to bending thereby articulating front portion 42 relative to rear portion 43, as shown.

Figure 3D:
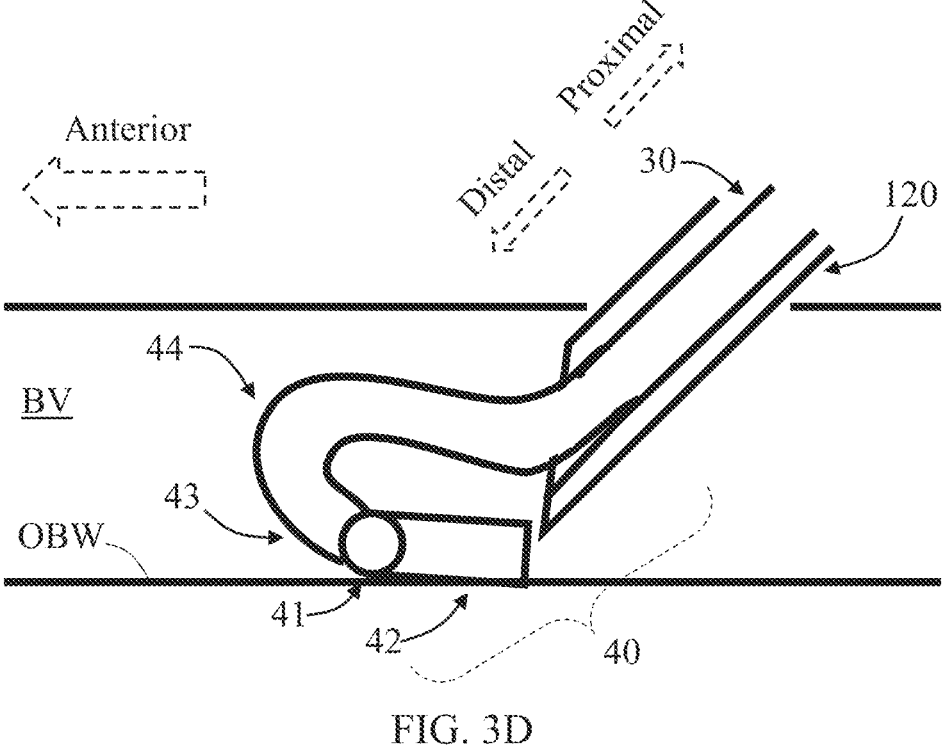

When the longitudinal compression of guidewire body 31 against a blood vessel wall exceeds a certain threshold (optionally predetermined threshold or within a predetermined range), when the articulation angle is between nominal positioning angle $\alpha_{nom}$ and minimally allowed articulation angle $\alpha_{min}$, tip segment 40 is configured to buckle into a buckled shape, above (proximally to) flexing portion 41, relative to remainder of the guidewire body 31 (FIG. 3D). As described earlier, buckling is set to occur before the compression force generated is sufficient to penetrate into blood vessel wall OBW. Tip segment 40 is configured to buckle, optionally in a chosen or predetermined orientation, such that an apex 44 of tip segment 40 in the buckled shape points anteriorly within blood vessel BV, away from the guidewire body 31 and blood vessel wall OBW.

Figure 3E:
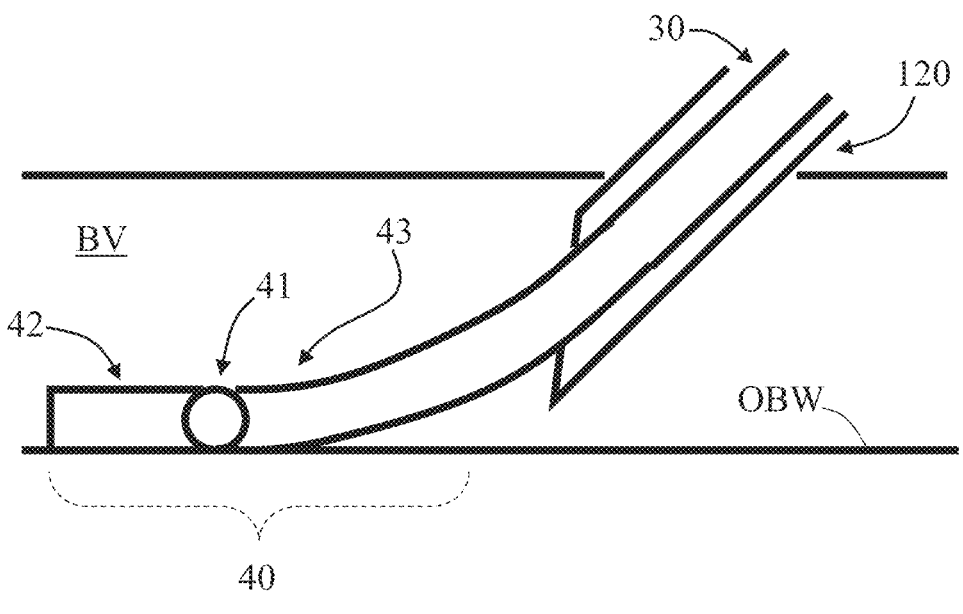

Furthermore, when rear portion 42 is substantially horizontal relative to blood vessel wall OBW and presses against it along most or all side length thereof, the pressure applied therethrough to blood vessel wall OBW is reduced. As such, the articulated front portion 42 is effectively serving as a stopper against further lateral progression towards opposing blood vessel wall OBW, thereby affecting anterior progression of more proximal portion of guidewire body 31 over apex 44. Upon further progress of guidewire 30 anteriorly into blood vessel BV, tip segment 40 can optionally bounce forward and regain a straighter form relative to blood vessel contour (as shown in FIG. 3E, for example).

FIGS. 4A-4E schematically illustrate several views representing possible other scenarios in execution of a method for delivering guidewire 30 using an exemplary vascular access technique. This series of scenarios relate to possible outcome and/or potential advantage of using guidewire 30 following unintentional penetration of blood vessel wall following insertion, which causes initial penetration of the guidewire into the blood vessel wall as it emerges from the access needle. Such occasions may be more prone to happen when using off the shelf needles like needle 20, unlike for example if using a dedicated kit comprising guidewire 30 and needle 120.

Figure 4A:
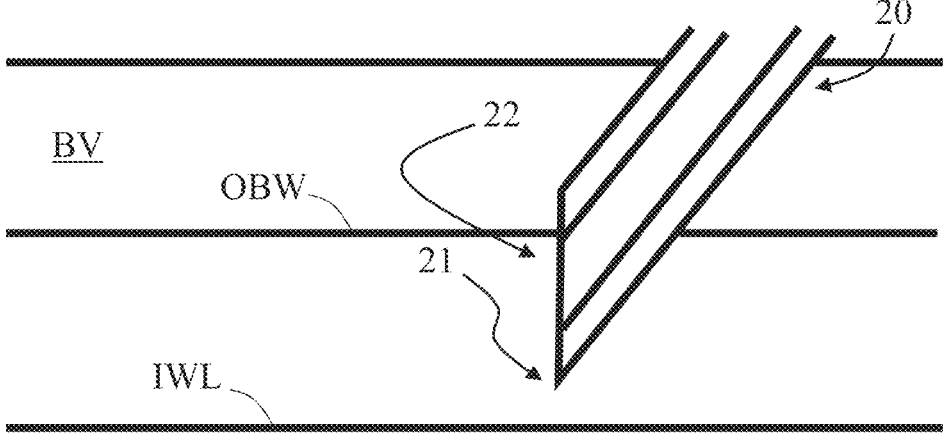
FIGS. 4A-4E schematically illustrate several views representing possible other scenarios in execution of a method for delivering the exemplary guidewire of FIG. 2 using an exemplary vascular access technique, according to some embodiments.
Figures 4B, 4C:
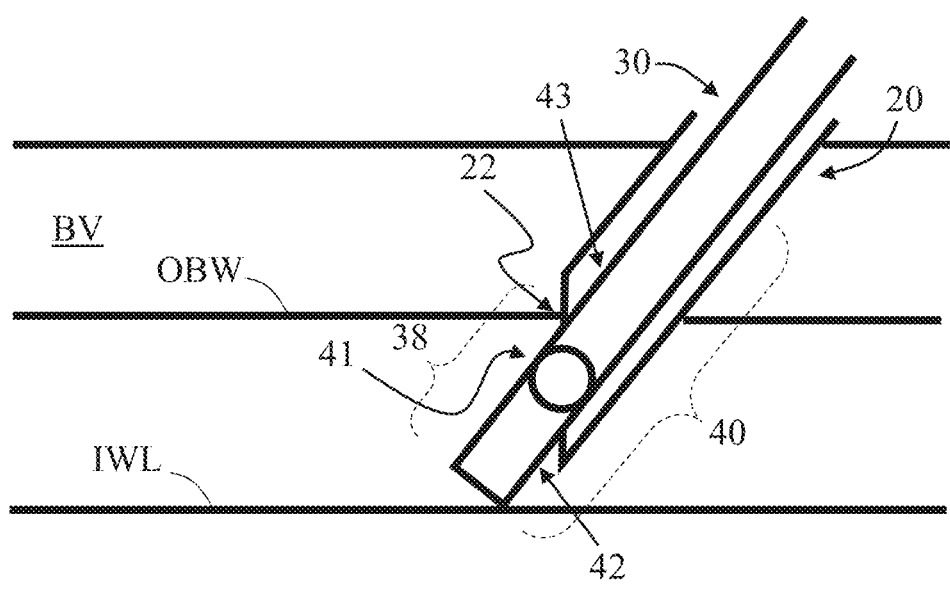

Needle 20 is inserted into blood vessel BV until and as shown needle tip 21 unintentionally penetrates opposing blood vessel wall OBW (FIG. 4A) and stops before an internal blood vessel wall layer IWL. Guidewire 30 is then introduced into needle 20 such that tip segment 40 protrudes via beveled opening 22 across needle tip 21 (FIG. 4B) until reaching internal wall layer IWL with flexing portion 41 located adjacent bevel opening 22. In such stage, when flexing portion 41 is free to allow articulation of front portion 42, the resistance to further advancement of needle tip segment 40 increases and causes articulation of front portion 42 relative to all other members including rear portion 43, rest of guidewire 30 and needle 20, as shown in FIG. 4C.

Figure 4D:
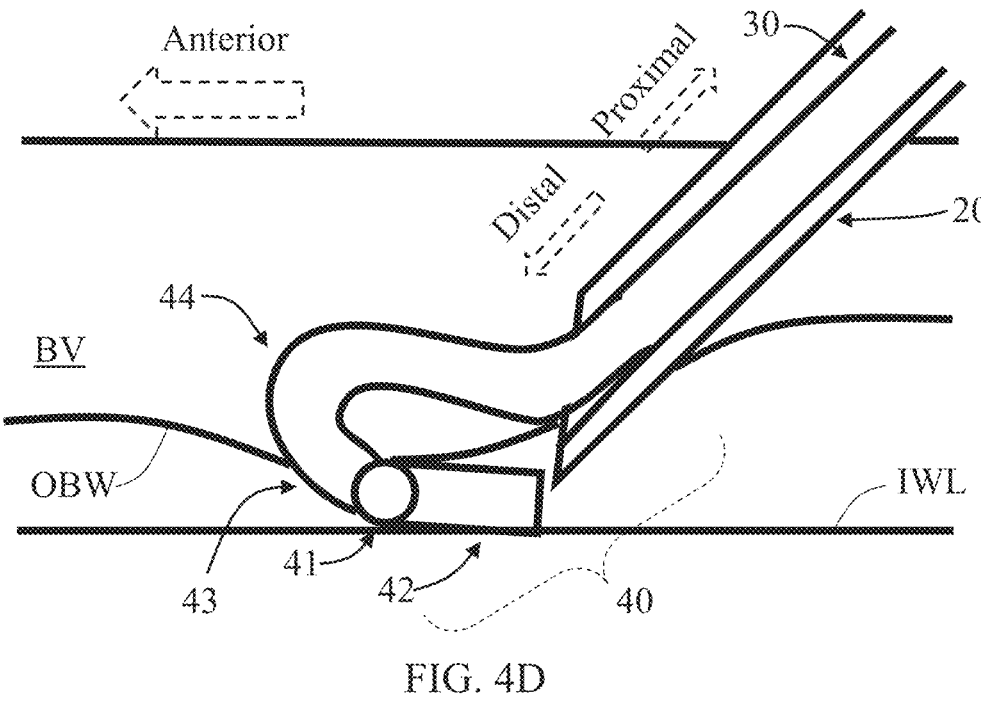

When the articulation angle is between nominal positioning angle $\alpha_{nom}$ and minimally allowed articulation angle $\alpha_{min}$, tip segment 40 is configured to buckle into a buckled shape, above (proximally to) flexing portion 41, relative to remainder of the guidewire body 31 (FIG. 4D). Guidewire tip segment 40 is configured such that buckling is set to occur before the reaching an axial force sufficient to penetrate further into opposing blood vessel wall OBW through inner wall layer IWL. Tip segment 40 is configured to buckle, optionally in a chosen or predetermined orientation, such that an apex 44 of tip segment 40 in the buckled shape points anteriorly within blood vessel BV, away from the guidewire body 31 and blood vessel wall OBW.

Figure 4E:
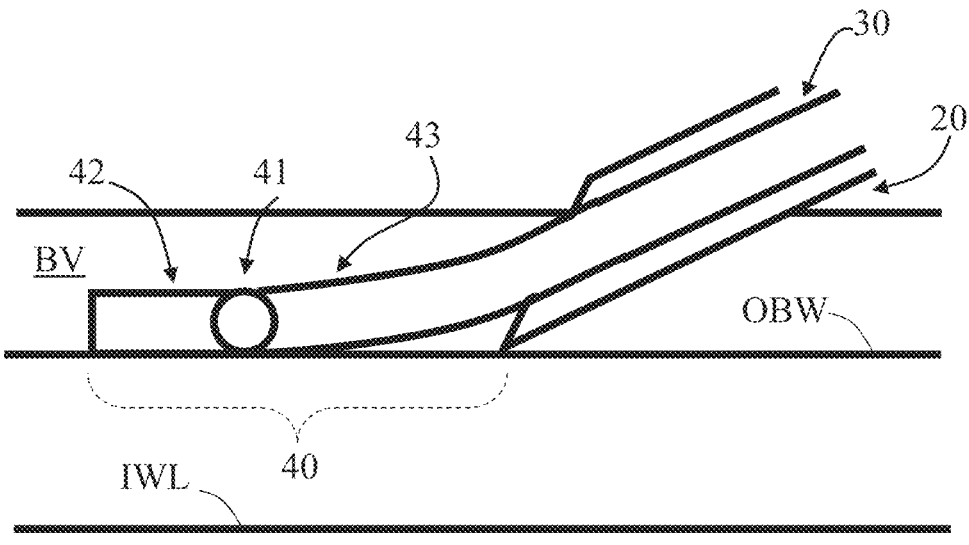

Furthermore, when rear portion 42 is substantially horizontal relative to inner wall layer IWL and presses against it along most or all side length thereof, the pressure applied therethrough to inner wall layer IWL is reduced. As such, the articulated front portion 42 is effectively serving as a stopper against further lateral progression towards opposing blood vessel wall OBW, thereby affecting anterior progression of more proximal portion of guidewire body 31 over apex 44. Upon further progress of guidewire 30 anteriorly into blood vessel BV, tip segment 40 can optionally bounce forward and regain a straighter form relative to blood vessel contour (as shown in FIG. 4E, for example).

Reference is made to FIGS. 5A-51 which illustrate cross-sectional side views of several exemplary variations of the guidewire 30. FIG. 4A shows a variation 50 of guidewire 30 with part of intermediate segment 35 and entire tip segment 40. Guidewire variant 50 comprises an elastic core member 51 extending along most or all length of the guidewire, optionally formed of metal alloy such as Ni—Ti alloy. Core member 51 is narrowed at second transition point 36 such that it is narrower along most or all length of guidewire tip segment 40 than along most or all length of guidewire intermediate segment 35. The portion of core member 51 extending along tip segment 40 is also eccentric to remainder portion of core member 51 extending along intermediate segment 35 and optionally also guidewire proximal segment 32. Core member 51 is at least partially embedded in a matrix 52 of flexible material along tip segment 40, with minimal resistance to buckling, such that overall cross section of tip segment 40 is concentric with the remainder length of core member 51 along the guidewire intermediate segment 35. Narrowing of the wire reduces the moment of inertia and therefore consequently reduces the buckling force upon longitudinal compression. Eccentricity, relative to the distance between centers and relative to the diameter of the wire creates an asymmetric structure, thus it can reduce the buckling force upon longitudinal compression and/or change the behavior from buckling to bending due to the moment created. Flexible matrix covering allows high bending ability with small radius while maintaining the wire general diameter.

Figure 5A:
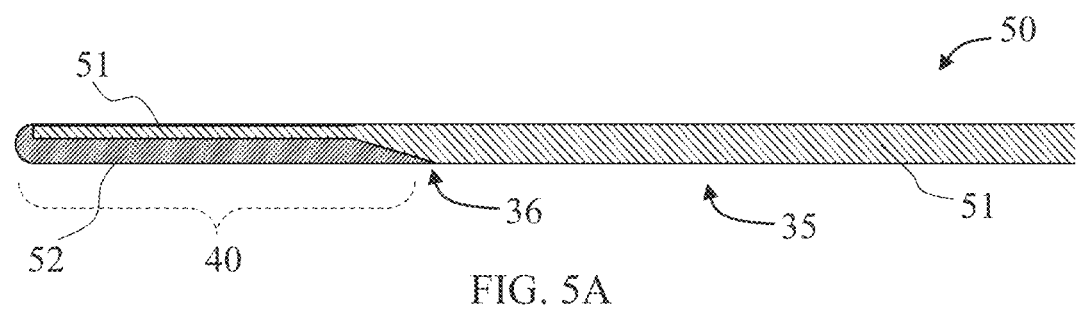
FIGS. 5A-5I illustrate cross-sectional side views of different exemplary variations for a distal portion of the exemplary guidewire of FIG. 2, according to some embodiments.
Figure 5B:
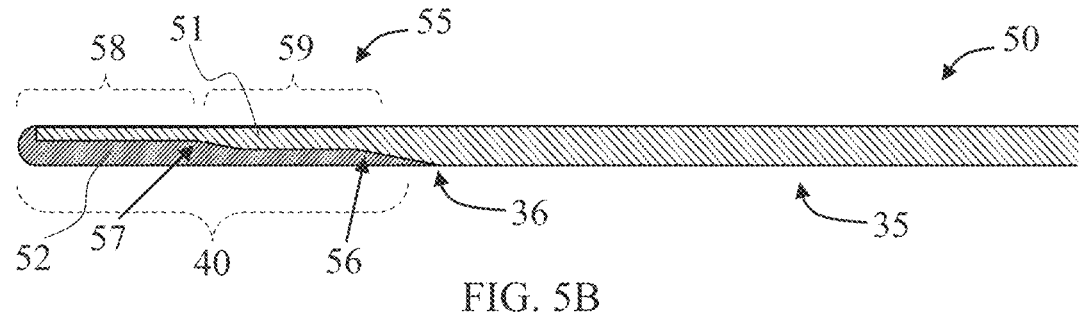
Figure 5C:
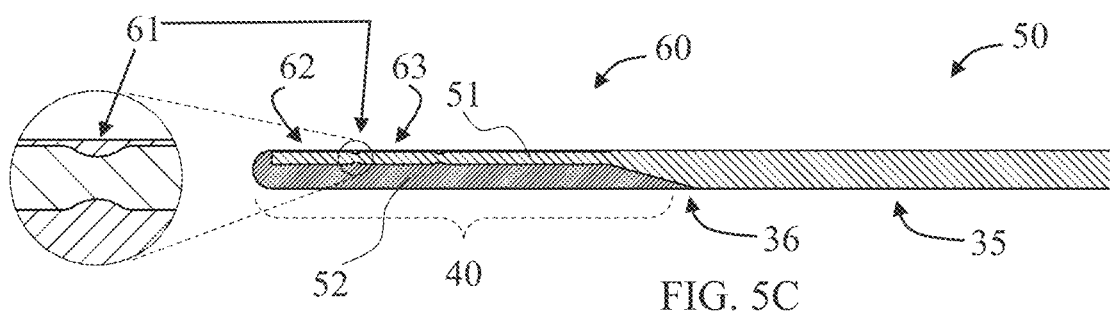

FIG. 5B shows a tip segment variation 55 of guidewire variation 50 in which tip segment narrows at two longitudinally spaced points 56 and 57, such that a distal portion 58 of tip segment 40 is more flexible and less resistant to buckling than a proximal portion 59 of tip segment, while proximal portion 59 is more flexible and less resistant to buckling than guidewire intermediate segment 35. FIG. 4C shows a tip segment variation 60 of guidewire variation 50 in which core member 51 has at least one flexing portion 61 in a form of a short indentation along tip segment 40, configured to facilitate or cause relative elastic articulation of adjacent portions 62 and 63 of tip segment 40 adjoined with flexing portion 61.

Figure 5D:
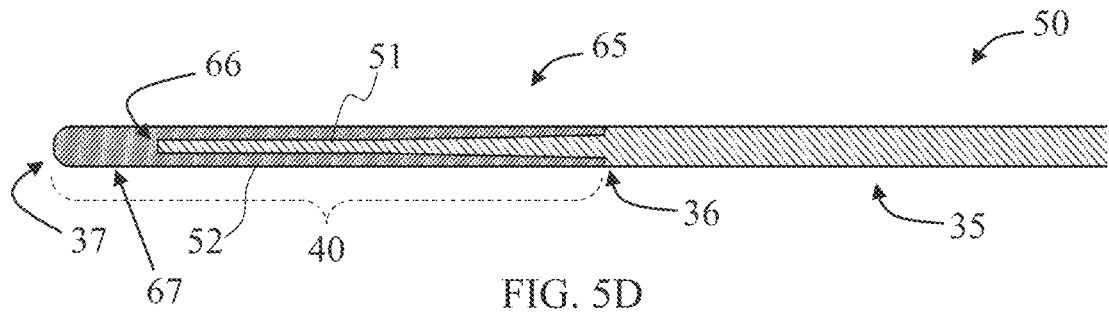

FIG. 5D shows a tip segment variation 65 of guidewire variation 50 in which core member 51 has a distal end 66 spaced apart from guidewire distal end 37, making such that the distal most portion 67 of tip segment 40 extending between core member distal end 66 and guidewire distal end 37 is occupied by matrix 52 only. Since that matrix 52 is substantially more flexible or malleable than core member 51 embedded in matrix 52, distal-most portion 67 is functionally configured as flexing portion 41 and facilitates elastic articulatbility about core member distal end 66 relative to remainder of tip segment 40.

Figure 5E:
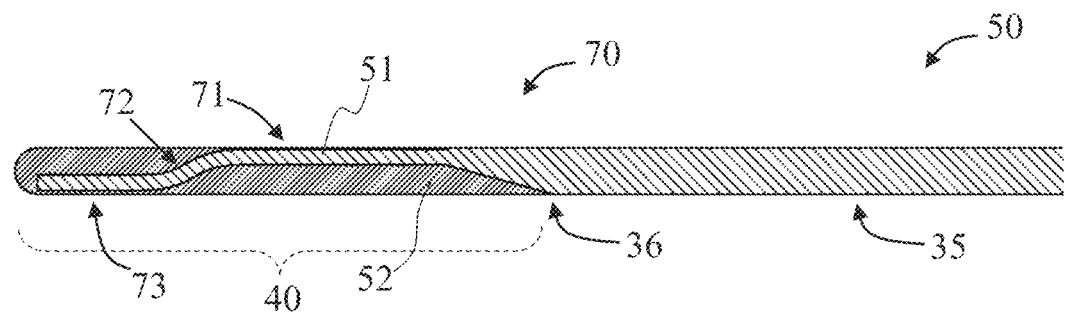

FIG. 5E shows a tip segment variation 70 of guidewire variation 50 in which the narrower portion of core member 51 extends straight eccentrically from guidewire intermediate segment 35 along a first side 71 of tip segment 40, curves at a curving portion 72 towards a second side 73 of tip segment 40, optionally opposing first side 71, end further extending straight eccentrically towards guidewire distal end 37 along second side 73 of tip segment 40. In this form, curving portion 72 is functionally configured as flexing portion 41 and/or the portion of tip segment 40 distal to curving portion 72 is functionally configured as articulating portion 42 relative to remainder portion of tip segment 40.

Figure 5F:
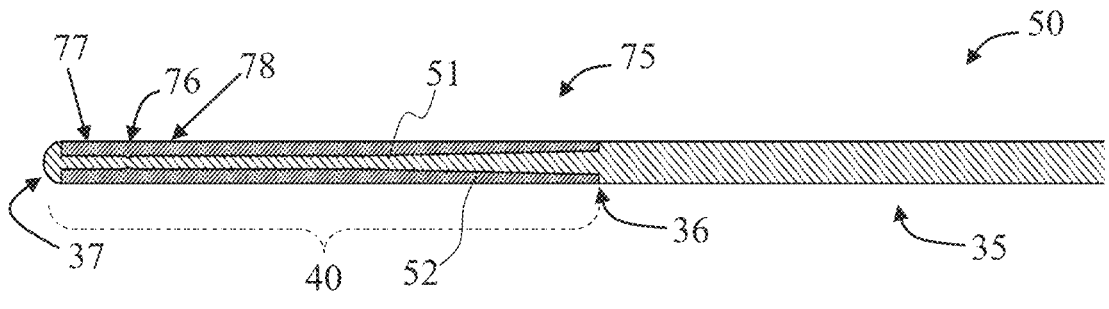

FIG. 5F shows a tip segment variation 75 of guidewire variation 50 in which the narrowed portion of core member 51 extends straight concentrically from guidewire intermediate segment 35 and continues to gradually narrow at least along part of tip segment 40 length. Core member 51 expands at guidewire distal end 37, optionally to outer diameter of guidewire intermediate segment 35, and forms a rounded tip of guidewire 30. Core member 51 has a flexing portion 76 on tip segment 40, optionally in a form of a slit or indentation, configured to facilitate or cause relative elastic articulation of adjacent portions 77 and 78 of tip segment 40 adjoined with flexing portion 76.

Figure 5G:
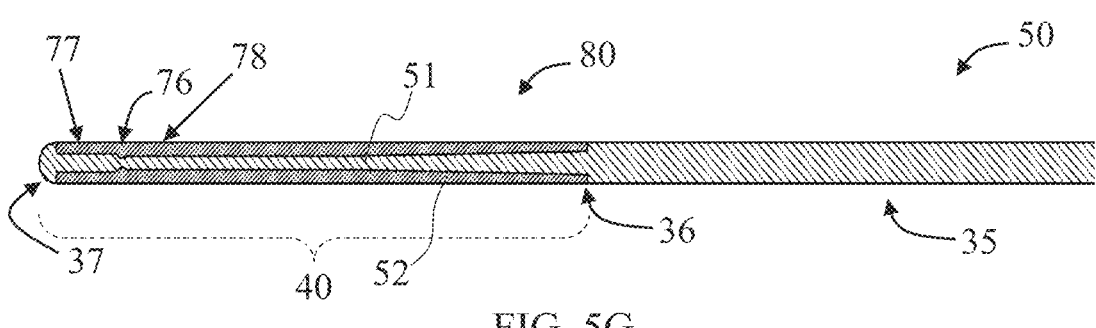
Figure 5H:
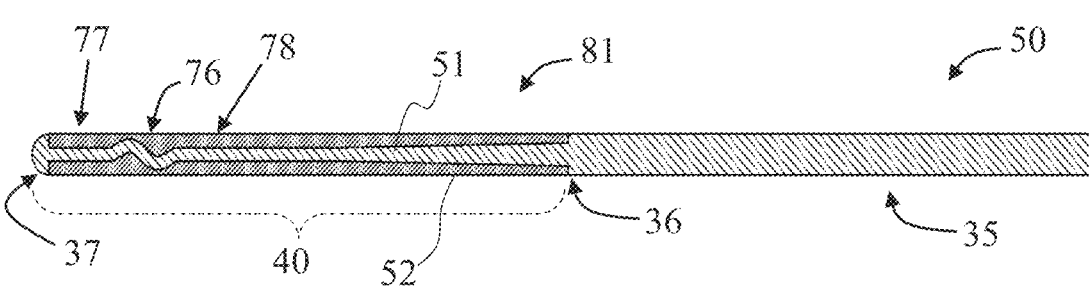
Figure 5I:
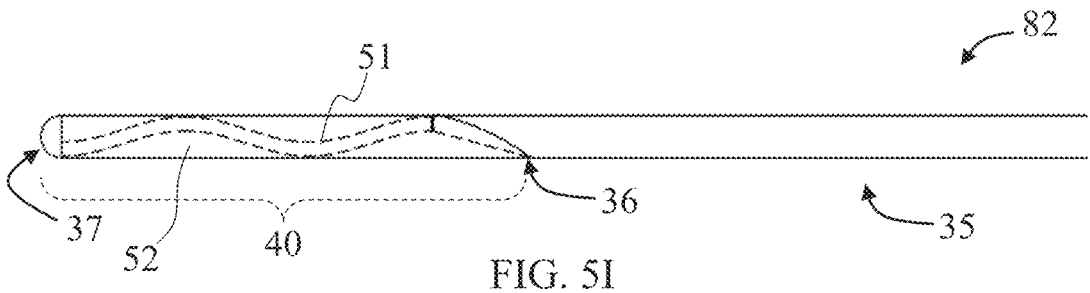

FIG. 5G shows a variation 80 of tip segment variation 75 in which core member 51 is thicker along distal-most portion 77 than along proximally adjacent portion 78 of tip segment 40, although still substantially thinner than core member diameter along guidewire intermediate segment 35. The difference in thickness affects the resistance of the wire to bend and thus prevents tip segment 75 from bending before segment 78 (as shown in FIG. 3D segment 42 is kept straight as opposed to segment 43 that is bended). FIG. 4H shows a different variation 81 of tip segment 75 in which flexing portion 76 is structurally and/or functionally configured as a coil or a spring. The coiled area defines the flexing portion and the bending mechanism in which the coiled area will compress and deflect sideways due to the forces generating within the spring.

FIG. 51 shows a variation 82 of guidewire 30 in which core member 51 along tip segment 40 is substantially narrower than along guidewire intermediate segment 35 and is helically wound from a side of tip segment 40 at second transition point 36 to an opposing side of tip segment 40 at guidewire distal end 37. Core member 51 is at least partially embedded in a matrix 52 along tip segment 40, with minimal resistance to buckling, such that overall cross section of tip segment 40 has same outer diameter as in remainder length of core member 51 along the guidewire intermediate segment 35. The helical structure of tip segment 40 significantly reduces its resistance to bending relative to a straight design.

Figure 6A:
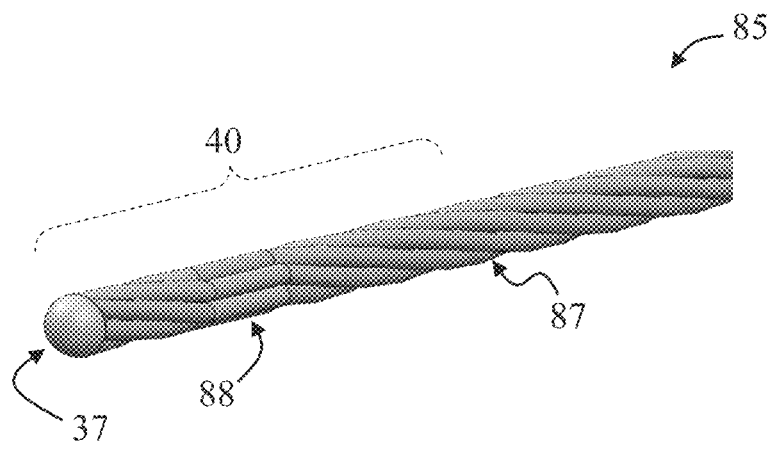
FIGS. 6A-6B illustrate, respectively, an isometric view and a side cross-sectional view of a first exemplary guidewire comprising a coiled member, according to some embodiments.
Figure 6B:
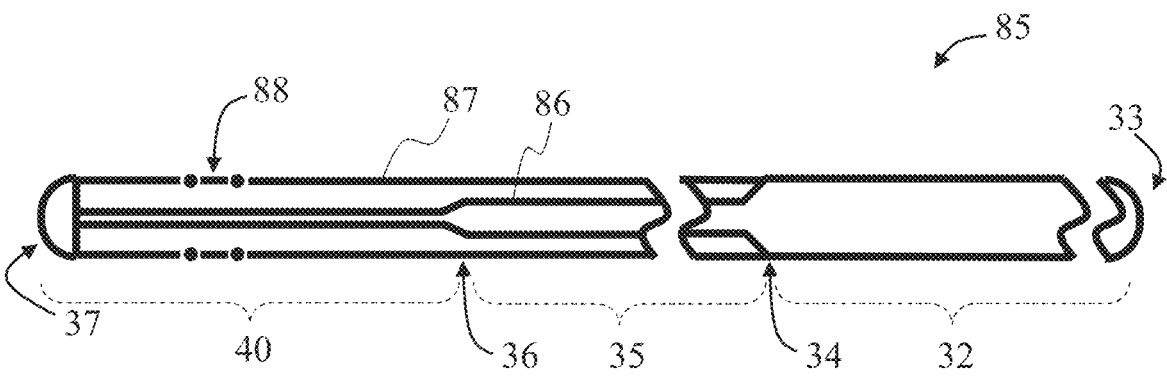

FIGS. 6A-6B illustrate, respectively, an isometric view and a side cross-sectional view of another exemplary variation 85 of guidewire 30. In this variation, guidewire 30 has an elastic core member 86 extending along most or all length of the guidewire, optionally formed of metal alloy such as Ni—Ti alloy. Core member 86 is narrowed at first transition point 34 such that it is narrower along most or all length of guidewire intermediate segment 35 than along length most or all length of guidewire proximal segment 32. Core member 86 is further narrowed at second transition point 36, such that it is narrower along most or all length of guidewire tip segment 40 than along most or all length of guidewire intermediate segment 35.

Core member 86 is covered with a cover element 87 along guidewire tip segment 40 and intermediate segment 35, having a maximal or average similar or identical to maximal or average diameter of guidewire proximal segment 35, such that guidewire 30 will have a generally constant diameter at least along most of its length. Cover element 87 includes a coiled member forming a coiled structure extending most or all length thereof. The coiled structure allows a better bending radius than a single wire having the same diameter while maintaining good flexibility characteristics and similar pushability. Cover element 87 has a local fixed deformation 88 of the coil structure configured as a fixed uncoiling or straightening of the coil structure. As such, fixed deformation 88 is functionally configured as flexing portion 41, for facilitating relative elastic articulation of adjacent portions 42 and 43 of the tip segment 40 separated with the fixed deformation 88.

Figures 7A, 7B, 8A, 8B, 8C, 8D:
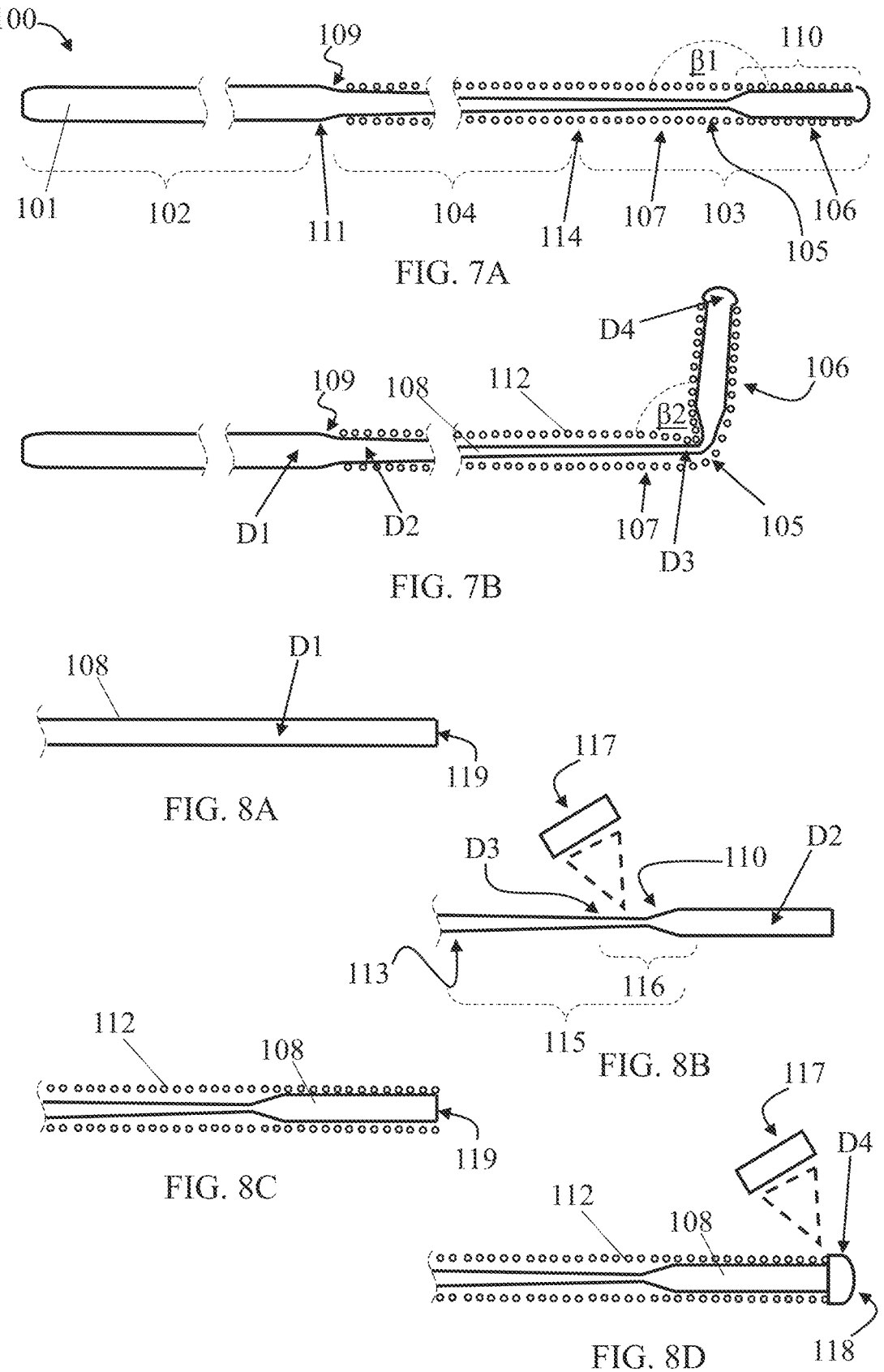
FIGS. 7A-7B schematically illustrate cross sectional side views of a second exemplary guidewire comprising a coiled member, before and after elastic articulation, according to some embodiments.
FIGS. 8A-8D schematically illustrate several views representing possible scenarios in execution of a method for forming the exemplary guidewire of FIG. 6A, according to some embodiments.

FIGS. 7A-7B schematically illustrate cross sectional side views of a guidewire 100 comprising a coiled member. Guidewire 100 is optionally a variation of guidewire 30 and similar thereto essentially and/or at least partially in structure, function and/or implementation, such as for example when performing the method along the exemplary scenarios as described with reference to FIGS. 3A-3E and/or FIGS. 4A-4E. Guidewire 100 includes a guidewire body 101 which comprises a guidewire proximal segment 102, a tip segment 103 and a guidewire intermediate segment 104 extending between and interconnecting or adjoining guidewire proximal segment 102 and tip segment 103. Resistance to bending of guidewire intermediate segment 104 along most or all length thereof is smaller than resistance to bending along most or all length of guidewire proximal segment 102.

Tip segment 103 includes a local flexing portion 105 having resistance to bending substantially smaller than the resistance to bending of guidewire intermediate segment 104, and of adjacent front portion 106 (extending to distally from flexing portion 105) and rear portion 107 (extending proximally from flexing portion 105) of tip segment 103, thereby affecting localized elastic articulatability of front portion 106 relative to rear portion 107 and/or to guidewire intermediate segment 104. Flexing portion 105 is configured to facilitate and cause elastically recoverable buckling of rear portion 107 upon sufficient longitudinal compression of the guidewire body 101 against a blood vessel wall, when front portion 106 is already articulated into inclining relative to the rear portion 107. Tip segment 103 is very short in length relatively to proximal segment 102 and to intermediate segment 104 of guidewire body 101 in order to substantially preserve overall required characteristics such as pushability along all guidewire body 101 and increased lateral flexibility along guidewire intermediate segment 104; however tip segment 103 has to be sufficiently long to facilitate both articulation of front portion 106 as well as buckling of rear portion 107 within treated blood vessel. In some embodiments, tip segment 103 is about 20 mm or less, optionally particularly about 10 mm or less, or optionally particularly about 5 mm or less, in total length. The total length of flexing portion 105 is optionally about 3 mm or less, optionally about 1 mm or less, or optionally about 0.5 mm or less, and it is distant (e.g., with center thereof) about 5 mm or less from a distal end of the guidewire body, optionally particularly about 1 mm or less. Flexing portion is optionally substantially equal in diameter to diameter of rear portion 107 and/or guidewire intermediate segment 104.

In some embodiments, flexing portion 105 is configured with variable resistance to bending which optionally increases when a articulation angle β, formed between front portion 106 and rear portion 107, reduces such as from first angle β1 when straighten (as shown in FIG. 7A) to second angle β2 when fully flexes (as shown in FIG. 7B). In some embodiments, when front and rear portions 106 and 107 are aligned, the resistance to bending of flexing portion 105 is smaller than resistance to penetration of a wall of the blood vessel with tip segment 103, so that front portion 106 will more likely articulate about flexing portion 105 rather than penetrate or continue penetrating unintentionally through the blood vessel wall, and, when flexed (i.e., articulation angle is substantially smaller then β1 and closer to β2), front portion 106 is configured to function as a stopper to resist further penetration. Second angle β2 is optionally the minimally allowed articulation angle β, and is optionally between 150° and 90°, optionally particularly between 135° and 95°. Tip segment 103 is configured such that, when articulation angle β is between first angle β1 and second angle β2, the force applied back from blood vessel wall in contact with distal end of guidewire body 101 generates internal stresses capable of causing or increasing likelihood of buckling of rear portion 107. In some such embodiments, the resistance to bending of flexing portion 105 is greater than the resistance to buckling of rear portion 107 of tip segment 103, when front and rear portions 106 and 107 form articulation angle β greater than first angle β1 such as the minimally allowed articulation (second) angle β2.

An elastic core member 108 extends along most or all length of the guidewire body 101, optionally though not necessarily made from a single material or extrusion, for example. Core member 108 is optionally formed of a shape memory and/or superplastic alloy such as Ni—Ti alloy, and it incorporates the flexing portion 105 along tip segment 103. Core member 108 may include at least one narrowing 109 at or adjacent to a first transition point 111 adjoining guidewire proximal segment 102 and guidewire intermediate segment 104. Narrowing 109 may be relatively steep (e.g., one or more inclined and/or step-like drops in diameter, for example). In some embodiments, distally from narrowing, core member 108 reduces continuously and gradually in diameter similar to a conical frustrum along length of guidewire intermediate segment 104 (as shown). Narrowing 109 reduces core member 108 diameter from a first core member diameter D1 proximally to narrowing 109 to a second core member diameter D2, smaller than first core member diameter D1, distally to narrowing 109. First core member diameter D1 is optionally substantially equal to overall outer diameter of guidewire body 101, optionally within a range of 0.2 mm and 1.2 mm, or optionally within a range of 0.3 mm and 0.6 mm, or optionally about 0.45 mm. First core member diameter D1 may be substantially constant along most or all length of guidewire proximal segment 102, including of first transition point 111. Second core member diameter D2 may be at least about 0.1 mm smaller than first core member diameter D1, and may be located a few millimeters or less, optionally about 1 mm or less, distally to first transition point 111.

Tip segment 103 adjoins guidewire intermediate segment 104 at a second transition point 114 and may continue the general conical until or across flexing portion 105 without a narrowing, as shown, however core member 108 may include a second narrowing at or adjacent to second transition point 114. Core member 108 also includes a widening 110 proximally to flexing portion 105, such that core member 108 increases in diameter from a third core member diameter D3 proximally to widening 110 to a fourth core member diameter D4 (being greater than third core member diameter D3) distally to widening 110. Third core member diameter D3 is optionally substantially smaller than second core member diameter D2, for example about 50% or less, optionally about third, of second core member diameter D2. Widening 110 may be relatively steep (e.g., one or more step-like rises in diameter, as shown), or it may be gradually inclining along front portion 106. Fourth core member diameter D4 is substantially equal to or smaller than first core member diameter D1, and it is optionally the maximal diameter of tip segment 103, optionally particularly of front portion 106 thereof.

Core member 108 is at least partially covered with a cylindrical coiled member 112 which extends between narrowing 109 and widening 110 (optionally from adjacent to narrowing 109 to adjacent to widening 110). Coiled member 112 has substantially constant outer diameter, and is substantially equal to first core member diameter D1 and/or to fourth core member diameter D4, such that overall diameter of guidewire body 101 is substantially constant and/or equal to first core member diameter D1, including along most or all length of the guidewire intermediate segment 104. Coiled member 112 is optionally formed of a spring and/or elastic metal alloy, such as stainless steel or gold plated tungsten for example, and is fixated with respective ends thereof to core member 108 at or adjacent to narrowing 109 and/or at or adjacent to widening 110.

FIGS. 8A-8D schematically illustrate several views representing possible scenarios in execution of a method for forming tip segment 103 of guidewire 100. A first optional scenario may include thinning a length portion 115 of core member 108 (shown before thinning in FIG. 8A), such as by way of grinding, so that it reduces in diameter along this length from first core member diameter D1 to thinner, optionally conical shape, having third core member diameter D3 proximally adjacent to widening 110 (as shown in FIG. 8B). The thinned length portion 115 is optionally equivalent to the length of tip segment 103 distally to flexing portion 105, optionally particularly to length of rear portion 107 thereof. Thinning length portion 115 of core member 108 reduces its resistance to bending and/or buckling along this length.

FIG. 8B also shows a second scenario in which flexing portion 105 is conditioned by way of local heat treatment focused to a target length 116 of core member 108 that is optionally equal to or smaller than about 5 mm, optionally particularly equal to or smaller than about 3 mm, or optionally particularly equal to or smaller than about 1 mm. The heat treatment may include use of laser heating, induction heating and/or Joule (e.g., direct current) heating. An exemplary laser heating may be continuous or applied as a plurality of laser pulses projected from a laser source 117 and directed accurately at the target length 116 at one side of, or around, core member 108. Optionally, the heat treatment is configured to elevate temperature of a portion of core member 108 along target length 116 to a chosen maximal temperature, such as to about 500° C. or less, during a chosen period, optionally of about 1 minute or less, optionally a few seconds in net total. The heat treatment is configured to increase flexibility of the treated area forming flexing portion 105, and therefore reduces its resistance to bending and optionally also increases its yield strength.

Following formation of flexing portion 105, coiled member 112 can be placed over core member 108 along the length of intermediate segment 104 and tip segment 103 (as shown in FIG. 8C) and then fixated thereto. Distal end of coiled member 112 may be fixated to core member 108 distally to flexing portion 105, optionally by way of adhesion, welding, riveting, soldering or brazing, optionally of a tip member 118 to free end 119 of core member 108 (as shown in FIG. 8D). Tip member 118 may have maximal outer diameter equal to or greater than outer diameter of coiled member 112 for preventing its release, and its maximal outer diameter is optionally equal to first core member diameter D1 and/or to fourth core member diameter D4. Proximal end of coiled member 112 may be fixated to core member 108, optionally adjacent to narrowing 109, such as by way of bonding using adhesives. In some embodiments, tip member 118 is welded to core member 108 and/or coiled member 112 using same laser source 117 previously applied for heat treatment to form flexing portion 105. Laser source 117 may be connected to a CAD system programmed to shift laser source 117 from a first position relative to core member 108 and from a first set of laser activation parameters required for the heat treatment process of target length, to a second position relative to core member 108 and to a second set of laser activation parameters required for the welding process of tip member 118.

EXAMPLE 1

The metal core of a guidewire was heat treated by laser applied in an approximately 1 mm diameter spot size with center approximately 3 mm from the distal end of the guidewire. The wire was rotated under the laser to heat treat the portion of the tip to create a section with higher flexibility.

The guidewire was then tested in an animal study dated Aug. 30, 2020. The guidewire was inserted into a test sheep vein at a greater than 60-degree angle from the horizontal. The guidewire insertion procedure was monitored under fluoroscopy during the insertion.

Figure 9A:
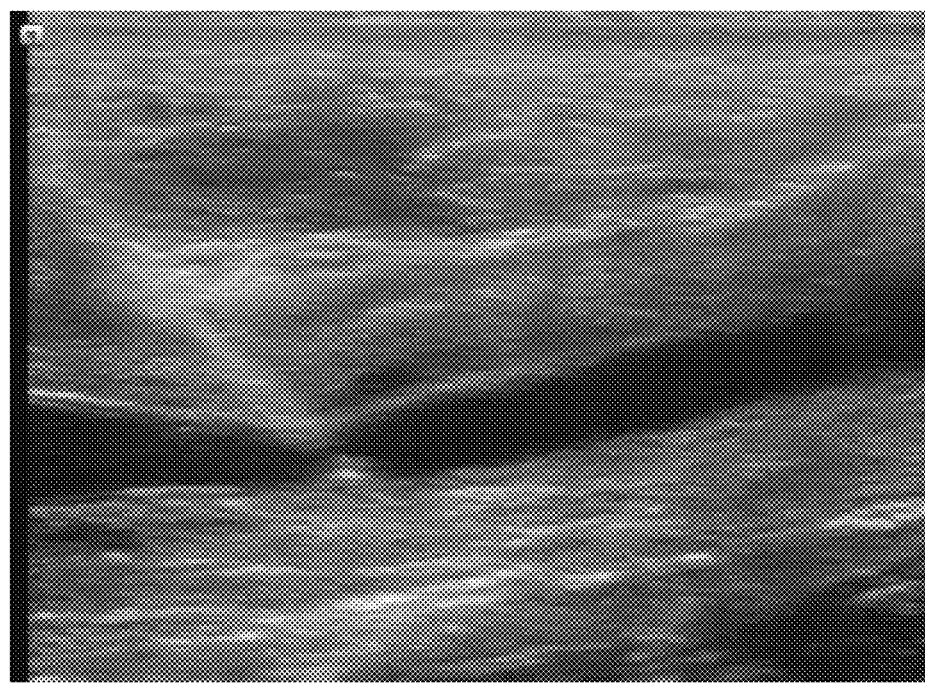
FIGS. 9A-9D are still images from a fluoroscopic movie of guidewire insertion according to some embodiments.
Figure 9B:
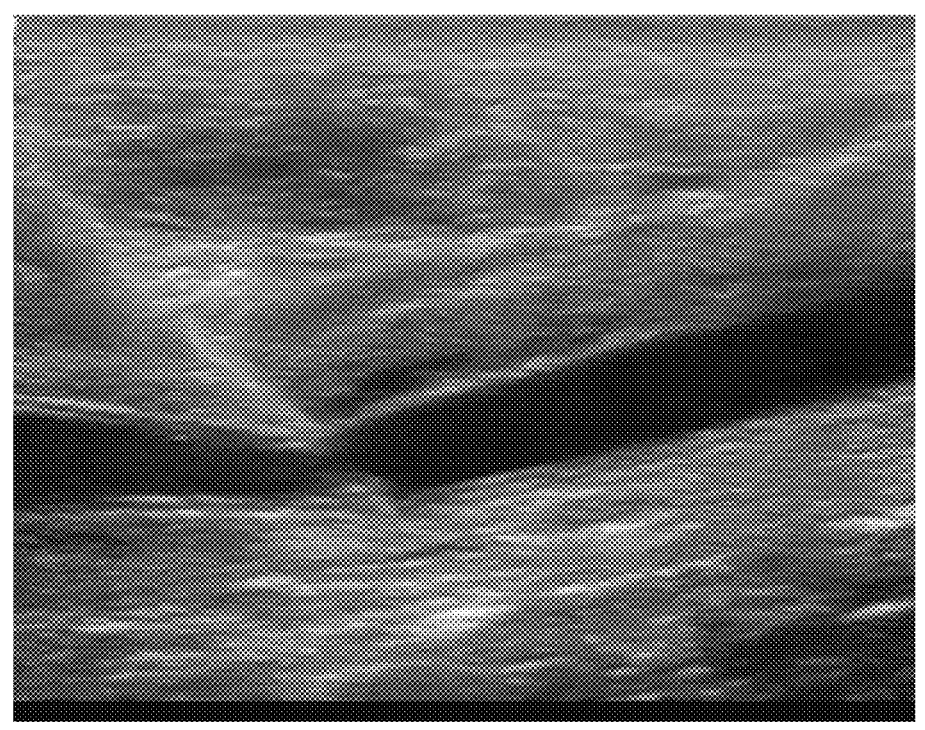
Figure 9C:
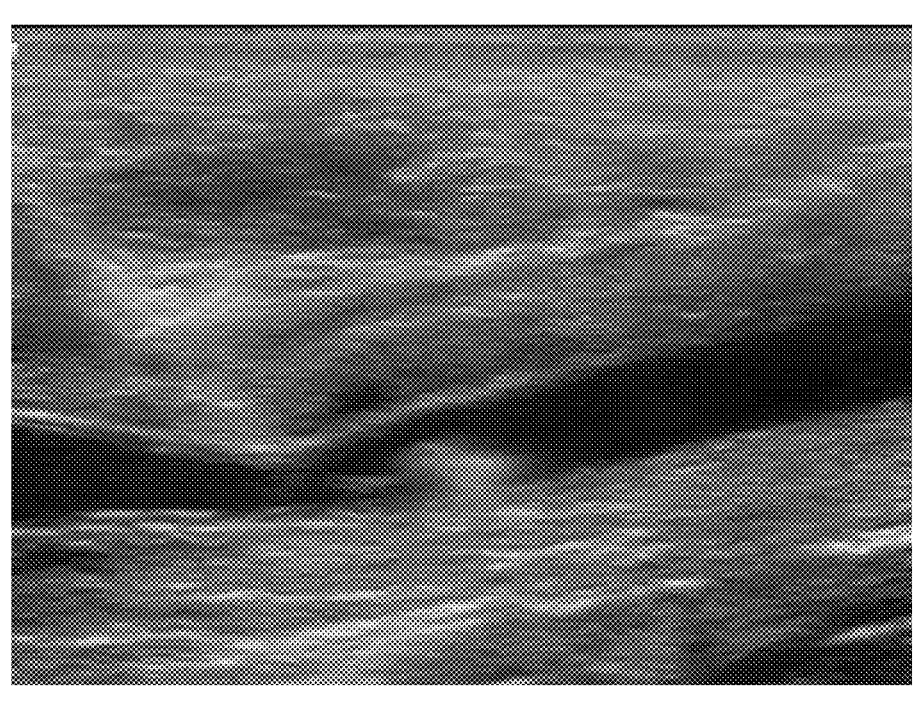
Figure 9D:
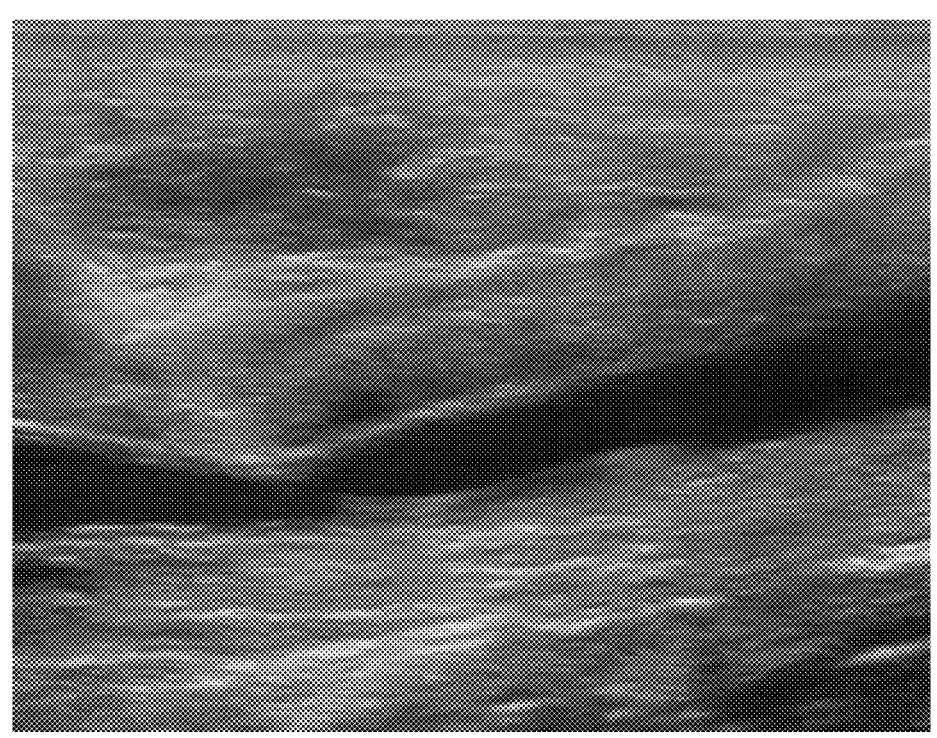

The results are illustrated in FIGS. 9A to 9D. FIG. 9A shows the guidewire as first introduced into the vein through the needle. In FIG. 9B the steep insertion force presses down onto the vein wall, forming a depression therein. FIG. 9C shows an elastic recovery of the guidewire tip as the guidewire buckling described above releases without puncturing the lower vein wall. FIG. 9D shows the guidewire deployed in the vein, ready to be advanced into the vasculature.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed disclosure.

Throughout this disclosure, a numerical value of a parameter, feature, characteristic, object, or dimension, may be stated or described in terms of a numerical range format. Such a numerical range format, as used herein, illustrates implementation of some exemplary embodiments of the disclosure, and does not inflexibly limit the scope of the exemplary embodiments of the disclosure. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the disclosure, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the disclosure which are illustratively described and presented in combination or sub-combination in the context or format of a single embodiment, may also be illustratively described and presented in the context or format of a plurality of separate embodiments.

Although the disclosure has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present disclosure. To the extent that section headings are used, they should not be construed as necessarily limiting.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A guidewire for transluminal routing of artifacts in a blood vessel, comprising:
   a guidewire body comprising an elastic core member extending along at least most of the length of the guidewire body, the guidewire body comprising a guidewire proximal segment, a tip segment and a guidewire intermediate segment extending between the guidewire proximal segment and the tip segment;
   wherein resistance to bending of the guidewire intermediate segment along at least most of the length thereof is smaller than resistance to bending along at least most of the length of the guidewire proximal segment;
   wherein the tip segment includes a local flexing portion having a resistance to bending smaller than (1) the resistance to bending of the guidewire intermediate segment, (2) of a front portion of the tip segment extending to distally from the local flexing portion, and (3) of a rear portion of the tip segment extending proximally from the local flexing portion, thereby affecting localized elastic articulatability of the front portion of the tip segment relative to the rear portion of the tip segment and/or to the guidewire intermediate segment;
   wherein the elastic core member has a diameter that reduces from a first diameter proximal to a narrowing to a second diameter smaller than the first diameter distal to the narrowing; and
   wherein the elastic core member comprises a widening proximal to the local flexing portion, wherein the widening increases the elastic core member diameter from a third diameter proximal to the widening to a fourth diameter greater than the third diameter distal to the widening.

2. The guidewire according to claim 1, wherein the local flexing portion is configured to facilitate and cause elastically recoverable buckling of the rear portion of the tip segment upon longitudinal compression of the guidewire body against a blood vessel wall, when the front portion of the tip segment is forcefully articulated relative to the rear portion of the tip segment.

3. The guidewire according to claim 1, wherein the tip segment is 20 mm or less in total length.

4. The guidewire according to claim 1, wherein the tip segment is 10 mm or less in total length.

5. The guidewire according to claim 1, wherein the tip segment is 5 mm or less in total length.

6. The guidewire according to claim 1, wherein the local flexing portion includes at least one of a slit, a joint, an indentation, a coiled segment, or any combination thereof.

7. The guidewire according to claim 1, wherein the third core member diameter is equal to or smaller than the second core member diameter and/or the fourth core member diameter is equal to the first core member diameter.

8. The guidewire according to claim 1, wherein the elastic core member is embedded in a matrix of flexible material between the narrowing and the widening of the elastic core member, such that an overall diameter of the guidewire body along at least most of the length of the guidewire intermediate segment is equal to the first diameter.

9. The guidewire according to claim 1, wherein the elastic core member is covered with a cylindrical coiled member between the narrowing and the widening of the elastic core member, such that an overall diameter of the guidewire body along at least most of the length of the guidewire intermediate segment is equal to the first diameter.

10. The guidewire according to claim 9, wherein the cylindrical coiled member is formed of a spring or elastic metal alloy and is fixated to the elastic core member at or adjacent to the narrowing or at or adjacent to the widening.

11. The guidewire according to claim 1, wherein the core member incorporates the flexing portion along the tip segment.

12. The guidewire according to claim 1, wherein the local flexing portion has a length along the guidewire body that is equal to or smaller than 5 mm.

13. The guidewire according to claim 1, wherein the local flexing portion has a length along the guidewire body of equal to or smaller than 3 mm.

14. The guidewire according to claim 1, wherein the local flexing portion is equal to or smaller than 1 mm.

15. The guidewire according to claim 1, wherein the elastic core member is formed of a selectively heat-treated shape memory alloy.

16. The guidewire according to claim 15, wherein a portion of the elastic core member is heat-treated by exposure to a temperature of about 500° C. or less during a period of about 1 minute or less.

17. The guidewire according to claim 16, wherein the exposure precedes fixation of a distal end of a coiled member to the elastic core member distally to the local flexing portion.

18. The guidewire according to claim 1, wherein the resistance to bending of the local flexing portion increases when an angle formed between the front portion of the tip segment and the rear portion of the tip segment reduces.

19. The guidewire according to claim 18, wherein a minimally allowed articulation angle between the front portion of the tip segment and the rear portion of the tip segment is between 150° and 90°.

20. The guidewire according to claim 19, wherein the minimally allowed articulation angle is between 135° and 95°.

21. The guidewire according to claim 1, wherein a total length of the local flexing portion is 0.5 mm or less.

22. The guidewire according to claim 1, wherein a diameter of the local flexing portion is equal to a diameter of the rear portion of the tip segment and/or to the guidewire intermediate segment.

23. The guidewire according to claim 1, wherein a center of the local flexing portion is 5 mm or less from a distal end of the guidewire body.

24. The guidewire according to claim 1, wherein a center of the local flexing portion is 1 mm or less from a distal end of the guidewire body.

25. A kit comprising:
  a guidewire comprising a guidewire body having a guidewire proximal segment, a tip segment and a guidewire intermediate segment extending between the guidewire proximal segment and the tip segment; and
  a needle comprising a beveled opening distally adjacent to a distal needle tip;
    wherein resistance to bending of the guidewire intermediate segment along at least most of the length thereof is smaller than resistance to bending along at least most of the length of the guidewire proximal segment;
  wherein the tip segment includes a local flexing portion having resistance to bending smaller than (1) the resistance to bending of the guidewire intermediate segment, (2) of a front portion of the tip segment extending to distally from the local flexing portion, and (3) of a rear portion of the tip segment extending proximally from the local flexing portion, thereby affecting localized elastic articulatability of the front portion of the tip segment relative to the rear portion of the tip segment and/or to the guidewire intermediate segment;
  wherein the beveled opening has a length configured such that when the front portion of the tip segment is pushed against a blood vessel wall, the front portion is configured to articulate about the local flexing portion upon axial protrusion from the beveled opening.

26. The kit according to claim 25, wherein the beveled opening is equal to or greater by up to 2 mm than the front portion in length.

27. The kit according to claim 25, wherein the beveled opening is equal to or smaller by up to 2 mm than the front portion in length.

28. A guidewire for transluminal routing of artifacts in a blood vessel, comprising:
  a guidewire body comprising a guidewire proximal segment, a tip segment and a guidewire intermediate segment extending between the guidewire proximal segment and the tip segment;
  wherein resistance to bending of the guidewire intermediate segment along at least most of the length thereof is smaller than resistance to bending along at least most of the length of the guidewire proximal segment;
  wherein the tip segment includes a local flexing portion having resistance to bending smaller than the resistance to bending of (1) the guidewire intermediate segment, (2) of a front portion of the tip segment extending to distally from the local flexing portion, and (3) of a rear portion of the tip segment extending proximally from the local flexing portion, thereby affecting localized elastic articulatability of the front portion of the tip segment relative to the rear portion of the tip segment and/or to the guidewire intermediate segment;
  wherein the resistance to bending of the local flexing portion is smaller than resistance to penetration of a wall of the blood vessel with the tip segment when the front portion of the tip segment and the rear portion of the tip segment are aligned, and/or
  wherein the resistance to bending of the local flexing portion is greater than a resistance to buckling of the rear portion of the tip segment when the front and the rear portions of the tip segment form a minimally allowed articulation angle therebetween.

29. The guidewire according to claim 28, wherein the local flexing portion is about 3 mm or less in length and distant about 5 mm or less from a distal end of the guidewire body.

30. The guidewire according to claim 28, wherein the resistance to bending of the local flexing portion is smaller than resistance to penetration of a wall of the blood vessel with the tip segment when the front portion of the tip segment and the rear portion of the tip segment are aligned.

31. The guidewire according to claim 29, wherein the resistance to bending of the local flexing portion is greater than a resistance to buckling of the rear portion of the tip segment when the front and the rear portions of the tip segment form a minimally allowed articulation angle therebetween.

* * * * *